(12) United States Patent
Sawada et al.

(10) Patent No.: US 9,824,189 B2
(45) Date of Patent: Nov. 21, 2017

(54) IMAGE PROCESSING APPARATUS, IMAGE PROCESSING METHOD, IMAGE DISPLAY SYSTEM, AND STORAGE MEDIUM

(71) Applicant: Panasonic Intellectual Property Management Co., Ltd., Osaka (JP)

(72) Inventors: Yoshihide Sawada, Kyoto (JP); Taichi Sato, Kyoto (JP); Hideto Motomura, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 107 days.

(21) Appl. No.: 14/979,724

(22) Filed: Dec. 28, 2015

(65) Prior Publication Data

US 2016/0217263 A1    Jul. 28, 2016

(30) Foreign Application Priority Data

Jan. 23, 2015 (JP) .................................. 2015-011136
Sep. 30, 2015 (JP) .................................. 2015-194410

(51) Int. Cl.
*G06F 19/00* (2011.01)
*G06T 3/40* (2006.01)
(Continued)

(52) U.S. Cl.
CPC ...... *G06F 19/3418* (2013.01); *G06F 3/04842* (2013.01); *G06F 19/321* (2013.01); *G06T 3/4053* (2013.01); *G06T 7/0012* (2013.01); *G06T 7/90* (2017.01); *G06T 2207/10056* (2013.01); *G06T 2207/20076* (2013.01); *G06T 2207/20081* (2013.01); *G06T 2207/30024* (2013.01)

(58) Field of Classification Search
USPC ................... 345/428, 660; 382/103; 348/143
See application file for complete search history.

(56) References Cited

U.S. PATENT DOCUMENTS 8,649,580 B2 * 2/2014 Yamamoto ......... G06K 9/00134
                                                      382/128
8,798,344 B2 * 8/2014 Kitamura .................. G06T 7/60
                                                      382/128
(Continued)

FOREIGN PATENT DOCUMENTS

JP         6-003601       1/1994
JP         2012-155455    8/2012
(Continued)

*Primary Examiner* — Kimbinh T Nguyen
(74) *Attorney, Agent, or Firm* — Wenderoth, Lind & Ponack, L.L.P.

(57) ABSTRACT

An image processing apparatus for estimating a position in an image which an operator who observes the image is likely to observe as the candidate of a next position is provided. The image processing apparatus includes a next observation estimating unit that estimates a position selected from among a plurality of positions using a parameter indicating an operation history and information regarding an estimation result at least at a current time on the basis of a probability value obtained from a predetermined probability distribution and a displayed image generating unit that generates an image to be displayed so that at least the candidate of the next position is visually recognizable.

18 Claims, 20 Drawing Sheets

(51) Int. Cl.
*G06T 7/00* (2017.01)
*G06F 3/0484* (2013.01)
*G06T 7/90* (2017.01)

(56) References Cited

U.S. PATENT DOCUMENTS

| | | | | |
|---|---|---|---|---|
| 8,879,813 | B1* | 11/2014 | Solanki | G06T 7/0014 382/128 |
| 2009/0180684 | A1* | 7/2009 | Tani | G06K 9/00134 382/162 |
| 2009/0190812 | A1* | 7/2009 | Sano | A61B 5/0059 382/128 |
| 2010/0250275 | A1* | 9/2010 | Sakagawa | G06F 19/321 705/2 |
| 2011/0205358 | A1 | 8/2011 | Aota et al. | |
| 2012/0188283 | A1 | 7/2012 | Ohashi | |
| 2012/0212599 | A1* | 8/2012 | Murakami | G02B 21/0036 348/79 |
| 2012/0327211 | A1* | 12/2012 | Yamamoto | G06F 19/366 348/79 |
| 2013/0051642 | A1* | 2/2013 | Kanda | G06T 7/0012 382/128 |
| 2013/0182901 | A1* | 7/2013 | Ishida | G06T 7/0012 382/103 |
| 2014/0301665 | A1* | 10/2014 | Saito | G06F 19/321 382/299 |
| 2016/0163048 | A1* | 6/2016 | Yee | G06T 7/11 382/131 |
| 2017/0109879 | A1* | 4/2017 | Urbano | G06T 7/0012 |

FOREIGN PATENT DOCUMENTS

| | | |
|---|---|---|
| JP | 2014-186496 | 10/2014 |
| WO | 2009/113265 | 9/2009 |

* cited by examiner

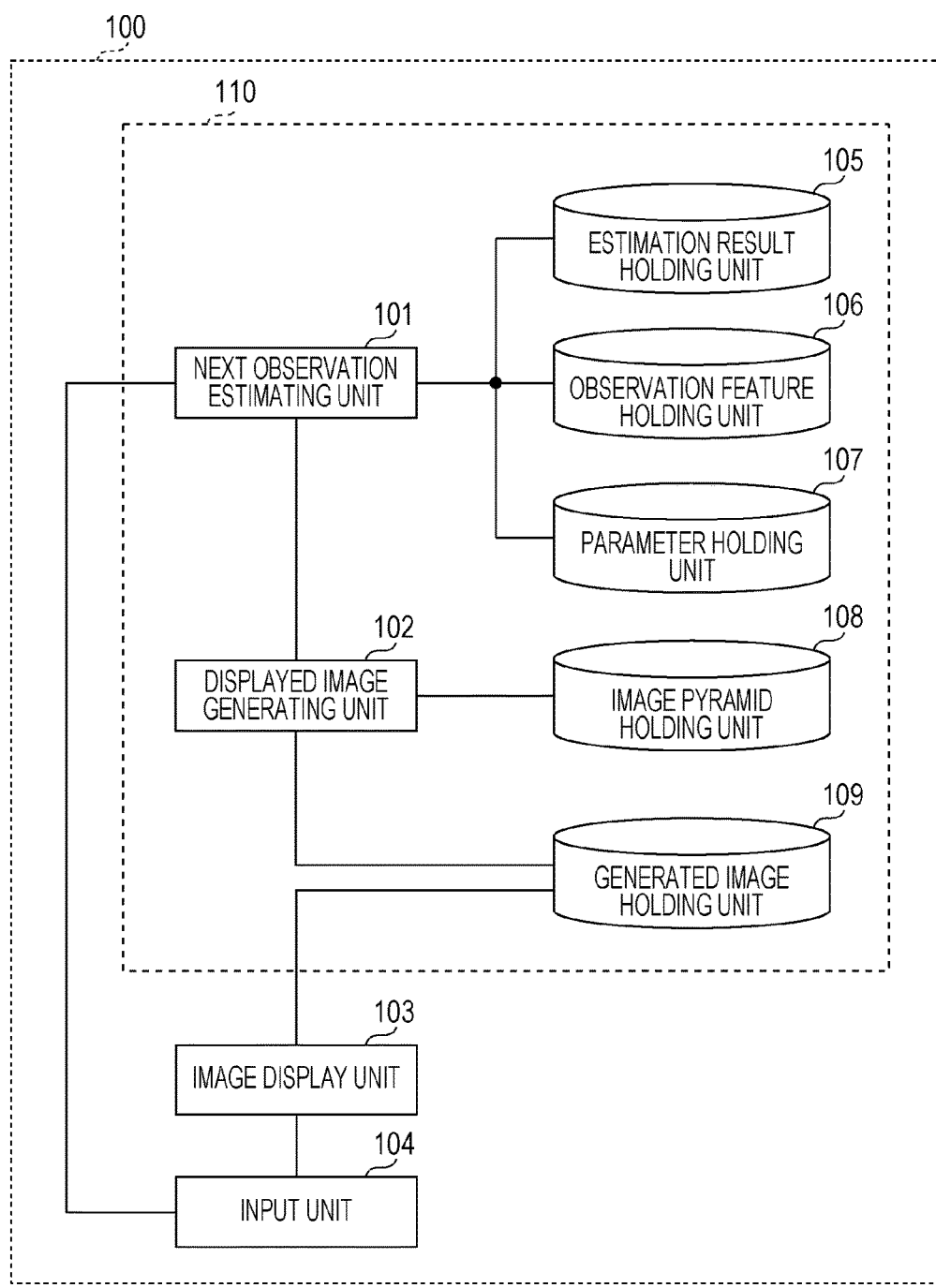

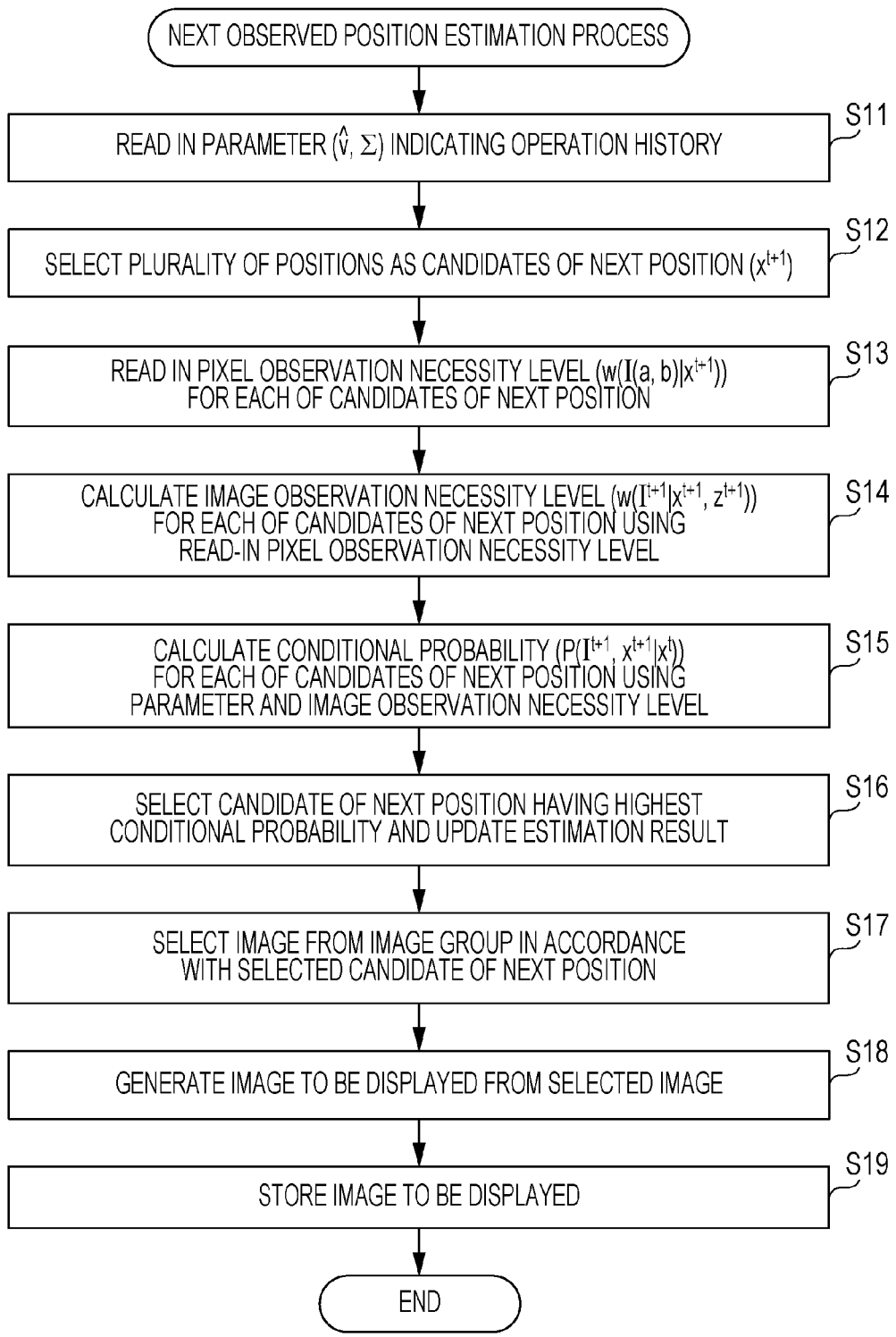

| 202 OBSERVATION TIME FIELD | 203 COORDINATE FIELD | 204 SCALE FACTOR FIELD |
|---|---|---|
| t - T | (1000, 1000) | 1.0 |
| t - T + 1 | (1050, 1000) | 1.5 |
| ... | ... | |
| t - 1 | (1200, 1400) | 3.0 |
| t | (1250, 1390) | 3.5 |

| 202 OBSERVATION TIME FIELD | 203 COORDINATE FIELD | 204 SCALE FACTOR FIELD |
|---|---|---|
| t - T + 1 | (1050, 1000) | 1.5 |
| t - T + 2 | (1055, 1000) | 1.5 |
| ... | ... | |
| t | (1250, 1390) | 3.5 |
| t + 1 | (1260, 1450) | 2.0 |

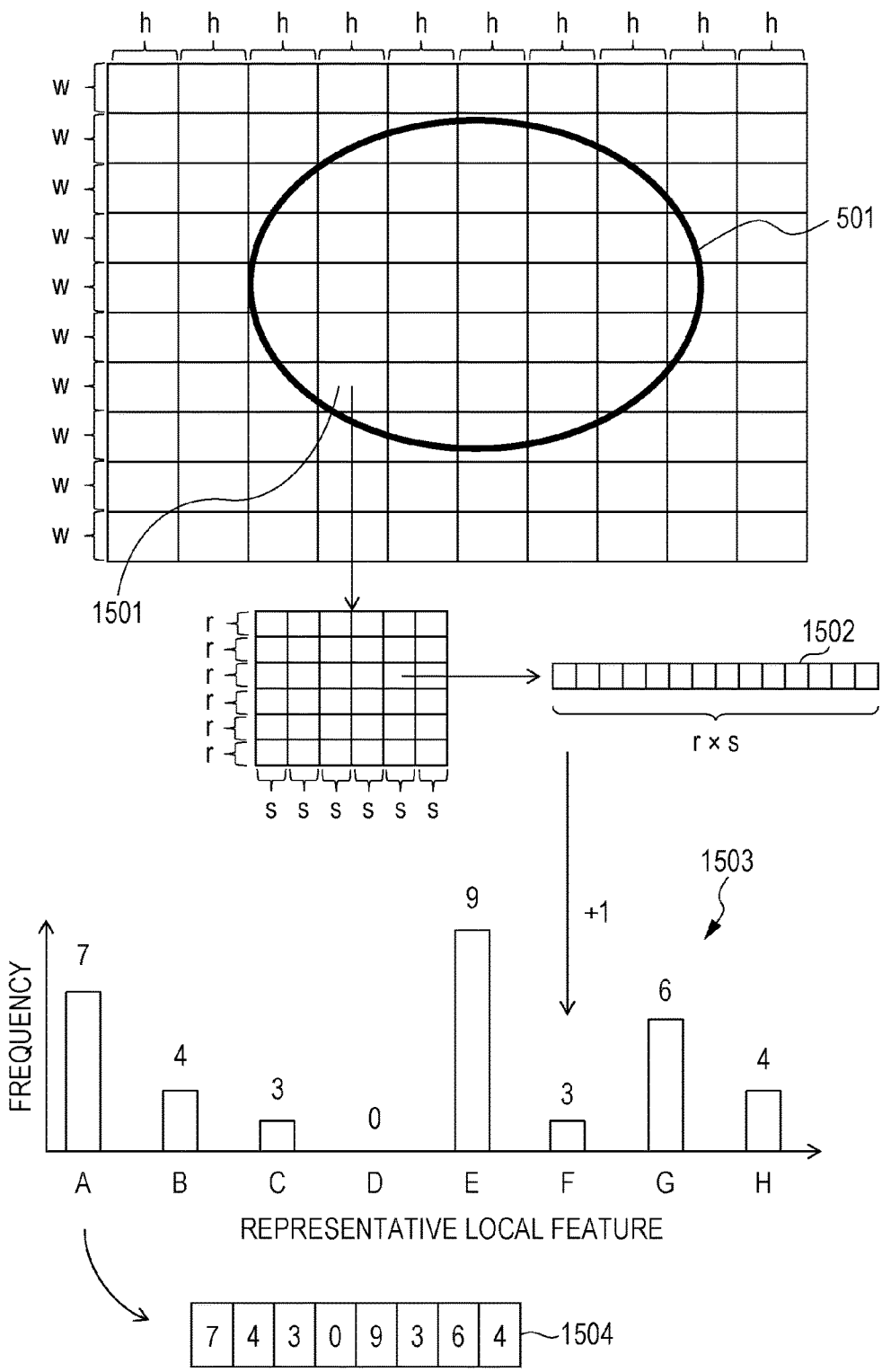

IMAGE PROCESSING APPARATUS, IMAGE PROCESSING METHOD, IMAGE DISPLAY SYSTEM, AND STORAGE MEDIUM

BACKGROUND

1. Technical Field

The present disclosure relates to a technology for changing the scale factor of an image.

2. Description of the Related Art

Pathology diagnoses have been made by pathologists who use a microscope. Recently, in many cases, due to the increase in pathology diagnosis and shortage of pathologists, it has been difficult to for a pathologist to make a diagnosis by using a microscope on site. Accordingly, the need for telepathology in which pathology specimen information is digitized, and an acquired image is sent to a remote location has been increasing. However, the sizes of pathological images increase since high-resolution pathological images are required. Accordingly, it is difficult to send the entire pathological image at one time.

For example, Japanese Unexamined Patent Application Publication No. 6-3601 describes a microscope still image transmission system in which a medical technologist in a hospital where no pathologist is available on site communicates an image with a pathologist while specifying the position and the scale factor of a region of a specimen to be observed in the image.

SUMMARY

In Japanese Unexamined Patent Application Publication No. 6-3601, the medical technologist needs to communicate with the pathologist in order to manually specify the position and the scale factor of the image to be observed. Accordingly, while the pathologist observes the image, the medical technologist needs to observe the image at the same time.

One non-limiting and exemplary embodiment provides an image processing technology for automatically estimating the position to be observed and the scale factor that the pathologist desires and automatically presenting the area of the image to the pathologist.

In one general aspect, the techniques disclosed here feature an image processing apparatus for estimating a position in an image which an operator who observes the image is likely to observe as the candidate of a next position. The image processing apparatus includes a next observation estimating unit that estimates a position selected from among a plurality of positions using a parameter indicating an operation history and information regarding an estimation result at least at a current time on the basis of a probability value obtained from a predetermined probability distribution and a displayed image generating unit that generates an image to be displayed so that at least the candidate of the next position is visually recognizable.

According to the present disclosure, the motion of a pathologist can be estimated by automatically estimating the observed position that the pathologist desires, and the area can be presented to the pathologist. That is, the observed position that the pathologist desires can be foreseen, and the pathologist can observe the area without the presence of a medical technologist.

It should be noted that general or specific embodiments may be implemented as a system, a method, an integrated circuit, a computer program, a computer-readable storage medium, or any selective combination thereof. Examples of the computer-readable storage medium includes a nonvolatile storage medium, such as a compact disc-read only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1 is a block diagram of the configuration of an image display system according to a first exemplary embodiment;

FIG. 2 is a flowchart illustrating the procedure for the operation performed by an image processing apparatus;

FIG. 3A illustrates a non-updated estimation result held by an estimation result holding unit;

FIG. 3B illustrates an updated estimation result held by the estimation result holding unit;

FIG. 7 illustrates the processing flow of the bag-of-features;

DETAILED DESCRIPTION

Figure 4:
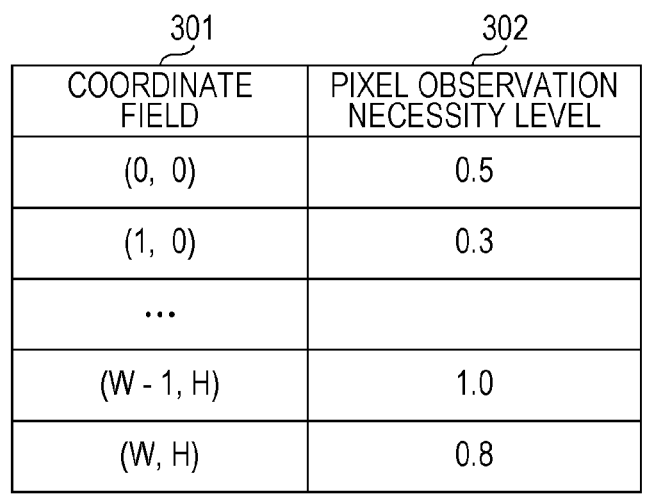
FIG. 4 illustrates the information that is held by an observation feature holding unit.

Underlying Knowledge Forming Basis of the Present Disclosure

The purpose of medical diagnosis business is to reach the name of a disease and the condition of the disease. The treatment policy is determined on the basis of the name of a disease or the condition of the disease that is finally determined. To determine the name of a disease or the condition of the disease, a pathological diagnosis is made. In the pathological diagnosis, a specimen is removed from the lesion, and the conditions of the specimen are observed on a cellular level. That is, in the pathological diagnosis, the removed specimen is sliced into layers of a thickness observable through a microscope. In this manner, a sample is generated. In recent years, the image of a sample has been captured by a digital camera or a scanner through a microscope and has been stored and referenced in the form of a digital image.

In addition, in recent years, due to the increase in pathology diagnosis and shortage of pathologists, it has been difficult for a pathologist to make a diagnosis by using a microscope on site. In such a case, telepathology is needed. That is, a person who is not a pathologist captures the image and sends the information about the image to the location at which a pathologist is available, and the pathologist located on the remote site makes a diagnosis. At that time, since the pathological image needs to be captured in high resolution (with a large number of pixels), the size of the image increases. Thus, it is difficult to send the entire image to the pathologist at one time. Accordingly, the specimen image needs to be divided into partial images, and the information regarding the partial images are sent.

In Japanese Unexamined Patent Application Publication No. 6-3601, a medical technologist collaborates with a pathologist and manually specifies the observed position and the scale factor. Accordingly, while the pathologist is observing the image, the medical technologist needs to work. The need for the presence of a medical technologist on site is one of the restrictions on a pathological diagnosis.

In general, instead of observing the entire specimen in detail, the pathologist observes the specimen from a higher perspective first and, thereafter, figures out a region to be observed in detail. Subsequently, the pathologist zooms in the image of the region on a display before observing the region. In this manner, the pathologist continuously changes a region to be displayed. If the pathologist finds an abnormal region displayed, the pathologist enlarges or reduces the image of the region and observes the region.

The present inventors conceived the following idea and started the research. That is, if the devices used for a pathological diagnosis are operated on the basis of the above-described operation pattern of pathologist s, the need for the presence of the medical technologist may be removed. As a result, the present inventors have developed a technology for pre-reading the position of a specimen which the pathologist wants to observe and presenting, to the pathologist, a partial image of the specimen which is estimated to be an image that the pathologist desires.

The aspects of the present disclosure are schematically described below.

According to an aspect of the present disclosure, an image processing apparatus for estimating a position in an image which an operator who observes the image is likely to observe as the candidate of a next position is provided. The image processing apparatus includes a next observation estimating unit that estimates a position selected from among a plurality of positions using a parameter indicating an operation history and information regarding an estimation result at least at a current time on the basis of a probability value obtained from a predetermined probability distribution and a displayed image generating unit that generates an image to be displayed so that at least the candidate of the next position is visually recognizable.

According to an embodiment of the present disclosure, the predetermined probability distribution is a Gaussian distribution, and the next observation estimating unit calculates a probability value of the conditional probability obtained using the Gaussian distribution for each of the plurality of positions in the image and estimates the position at which the highest probability value is obtained as the candidate of the next position.

According to an embodiment of the present disclosure, the parameter indicating the operation history includes at least information indicating the observed position in the image, and the next observation estimating unit considers each of the plurality of positions to be a candidate of a position likely to be observed next and calculates the probability value for each of the plurality of positions.

According to an embodiment of the present disclosure, the parameter indicating the operation history further includes information indicating a scale factor, and the next observation estimating unit calculates the probability values of a position likely to be observed next in the image and the scale factor for each of the plurality of positions.

According to an embodiment of the present disclosure, the next observation estimating unit calculates an image observation necessity level of each of small areas each including one of the plurality of positions using information regarding a pixel observation necessity level that is provided in advance for each of pixels of the image and that indicates the degree of necessity for observing the pixel, and the next observation estimating unit calculates the probability value using the predetermined probability distribution and the image observation necessity level calculated for each of the plurality of positions.

According to an embodiment of the present disclosure, the next observation estimating unit calculates the probability value for each of the plurality of positions in the image by further using information regarding an image feature calculated in advance.

According to an embodiment of the present disclosure, the displayed image generating unit generates an image used to display a plurality of results of estimation that are sequentially obtained.

According to an embodiment of the present disclosure, the image processing apparatus further includes a super-resolution processing unit that determines whether a super-resolution process is performed on a partial image including the candidate of the next position estimated by the next observation estimating unit. If the next observation estimating unit determines that the super-resolution process is to be performed, the super-resolution processing unit generates a magnified image having an increased number of pixels on the basis of data of a plurality of images of a given pathological specimen captured while lighting the pathological specimen from different directions and performs the super-resolution process based on deconvolution on the small area corresponding to the partial image of the magnified image.

According to another aspect of the present disclosure, an image display system includes any one of the above-described image processing apparatuses and an image display unit that displays the image generated by the displayed image generating unit.

According to still another aspect of the present disclosure, an image display system includes the above-described image processing apparatus that calculates the probability value for the scale factor, an image display unit that displays the image generated by the displayed image generating unit, and a result display control unit that performs control so that information regarding the position estimated by the next observation estimating unit and the scale factor is displayed.

According to an embodiment of the present disclosure, the image processing apparatus of the image display system further includes a super-resolution processing unit that determines whether a super-resolution process is performed on a partial image including the candidate of the next position estimated by the next observation estimating unit. If the next observation estimating unit determines that the super-resolution process is to be performed, the super-resolution processing unit generates a magnified image having an increased number of pixels on the basis of data of a plurality of images of a given pathological specimen captured while lighting the pathological specimen from different directions and performs the super-resolution process based on deconvolution on the small area corresponding to the partial image.

According to an embodiment of the present disclosure, the image display unit displays an area subjected to a super-resolution process performed by the super-resolution processing unit so that the area is visually recognizable.

According to an embodiment of the present disclosure, the image display system further includes an input unit that receives, from an operator, selection of a region in the image. If the input unit receives selection of a region in the image, the result display control unit instructs the next observation estimating unit to newly estimate the candidate of the next position using the selected region.

According to an embodiment of the present disclosure, when the input unit receives selection of a region in the image and if the selected region is not subjected to the super-resolution process, the result display control unit instructs the super-resolution processing unit to perform the super-resolution process on the selected region.

According to an embodiment of the present disclosure, the image display system further includes a magnifying operation determination unit that determines whether the operator has successively performed a predetermined number or more of magnifying operations on the region in the image. If determining that the operator has successively performed a predetermined number or more of a magnifying operation, the magnifying operation determination unit instructs the super-resolution processing unit to perform the super-resolution process on the region.

According to yet still another aspect of the present disclosure, an image processing method for estimating a position in an image which an operator who observes the image is likely to observe as a candidate of a next position is provided. The method includes estimating a position selected from among a plurality of positions using a parameter indicating an operation history and information regarding an estimation result at least at a current time on the basis of a probability value obtained from a predetermined probability distribution and generating an image to be displayed so that at least the candidate of the next position is visually recognizable.

According to yet still another aspect of the present disclosure, a non-transitory computer-readable recording medium storing a program is provided. The program causes an apparatus including a processor to perform a process to estimate a position in an image which an operator who observes the image is likely to observe as a candidate of a next position. The process includes estimating a position selected from among a plurality of positions using a parameter indicating an operation history and information regarding an estimation result at least at a current time on the basis of a probability value obtained from a predetermined probability distribution and generating an image to be displayed so that at least the candidate of the next position is visually recognizable.

According to yet still another aspect of the present disclosure, an image processing method includes obtaining a plurality of position candidates for a first position included in a first area, where the plurality of position candidates includes a first position candidate, the plurality of position candidates are included in a second area other than the first area, the first area and the second area are included in a first image, the second area includes a plurality of areas including a third area, the plurality of areas and the plurality of position candidates have a one-to-one correspondence, each of the plurality of areas includes the corresponding position candidate, the third area corresponds to the first position candidate, and the third area includes the first position candidate. The method further includes determining image feature information regarding a plurality of pixel values of pixels included in each of the plurality of areas, where the determination of the image feature information includes determination of the image feature information regarding the first pixel values included in the third area, obtaining history information indicating history of changing observed points for one or more images other than the first image, and determining one of the plurality of position candidates based on the image feature information and the history information. The plurality of pixel values of pixels included in each of the plurality of areas are classified by using a classification method corresponding to a type of the first image. The image feature information regarding the plurality of pixel values of the pixels included in each of the plurality of areas is determined based on the classification result. The first pixel values are classified by using the classification method corresponding to the type of the first image and a first classification result is obtained, and the image feature information regarding the first pixel values is determined based on the first classification result.

According to an embodiment of the present disclosure, the number of the first plurality of pixel values is $(p \times r) \times (q \times s)$, where p, q, r, and s are natural numbers. When the first pixel values are classified using the classification method corresponding to the type of the first image, the classification is performed for each of groups each including $(r \times s)$ pixel values to obtain $(p \times q)$ results of classification, and each of the obtained $(p \times q)$ results of classification is defined as the image feature information regarding one of the first pixel values.

Definition of Terms

As used herein, the following terms are defined as follows.

"Resolution" means the detail clarity of a captured image expressed by the number of pixels that form the image. If the image is rectangular in shape and has the number of pixels P in the horizontal direction and the number of pixels Q in the vertical direction, the image is also called "Image having a resolution of P×Q". For color images in which the color of a pixel is expressed using three types of sub-pixel, that is, red, green, and blue sub-pixels (a sub-pixel group), the total number of pixels constituted by the sub-pixel groups represents the resolution, instead of the total number of the sub-pixels. Note that "resolution" can be also defined for display apparatuses using, for example, dot per inch (DPI). However, to avoid confusion, as used herein, the term "resolution" is defined in relation to the number of pixels of an image.

"Scale factor" means the magnification percentage or the reduction percentage of a captured image used when the image is displayed on a display unit (a display). As used herein, the scale factor is "1 (=100%)" if the pixels of an image are displayed so as to have one-to-one correspondence to the pixels of the display unit (known as a "dot-by-dot" display mode). The scale factor is a parameter used to adjust the size of an image displayed on the display unit. The scale factor can be set for each of the vertical direction and horizontal direction of the image. Note that even when the scale factor is increased or decreased, the resolution of the displayed image remains unchanged.

A relationship between the resolution and the scale factor is described below in relation to the above-described definitions.

The case in which a given area of an image is zoomed in by a factor of R and displayed. If the original image is zoomed in by a factor of R, the perceived image clarity decreases to, for example, 1/R of the original image clarity. This is because the original image is zoomed in although the spatial frequency remains unchanged. In such a case, according to the exemplary embodiment described below, the area is displayed using the image of the same object captured at a resolution that is R times the original resolution. If the image captured at exactly R times the original resolution is not present, an image captured at, for example, S times the original resolution (S is greater than R) is selected. Thereafter, the image is multiplied by R/S, that is, is reduced. Alternatively, an image captured at, for example, S times the original resolution (S is the smallest next to R) is selected and, thereafter, is multiplied by S/R, that is, is enlarged. As a result, an image having a resolution that is R times the resolution of the original image can be obtained. To reduce an image, any widely known algorithm can be employed. In the following exemplary embodiments, description of the above-described process is not repeated. After the scale factor is obtained, an image having a resolution corresponding to the scale factor is selected. Thereafter, an enlargement process or the reduction process is performed as needed.

First Exemplary Embodiment

An image display system according to the present exemplary embodiment is described below. The image display system estimates the position of an area in an image the pathologist is subsequently interested in and the scale factor of the image on the basis of the feature that includes the image feature and, thereafter, displays the area of the image at the position with the scale factor is described below.

FIG. 1 is a block diagram of the configuration of an image display system 100 according to the first exemplary embodiment.

The image display system 100 includes an image processing apparatus 110, an image display unit 103, and an input unit 104. The image processing apparatus 110 includes a next observation estimating unit 101, a displayed image generating unit 102, an estimation result holding unit 105, an observation feature holding unit 106, a parameter holding unit 107, an image pyramid holding unit 108, and a generated image holding unit 109.

The image display system 100 and, in particular, the operation performed by the image processing apparatus 110 is schematically described below. In addition, the functions of the constituent elements of the image processing apparatus 110 and the information held (stored) by the image processing apparatus 110 are described together with the description of the operation.

FIG. 2 is a flowchart illustrating the procedure for the operation performed by the image processing apparatus 110.

In step S11, the next observation estimating unit 101 reads in parameters ($\hat{v}$, Σ) indicating the operation history from the parameter holding unit 107. The term "parameters indicating the operation history" refers to parameters indicating the operation history performed by an operator and collected in advance. An example of the operator is a set of a variety of pathologists or the pathologist who currently operates the system. The following description is given with reference to the operation history performed by a pathologist of any type.

As used herein, "$\hat{v}$" is pronounced "v hat". In equations described below, "^" is written above "v". "^" indicates the average of operations "v" obtained when the variety of pathologists perform observation. The operation "v" includes information for identifying the observed position in an image specified by each of the pathologists or the same pathologist and information regarding the scale factor specified in the observation. By expressing the information regarding the observed position in an image and the information regarding the scale factor of the image side by side, the operation "v" can be regarded as a vector. That is, "v" can be referred to as an "operation vector".

The operation vector is described below with reference to an example. Let (a, b) denote the position in an image to be observed, and let z denote the scale factor when the image is observed. The position (a, b) is, for example, the position of a pixel of an image displayed on a display and specified by the pathologist using, for example, a mouse. The scale factor z is the display magnification specified using a mouse or a keyboard. Then, the operation vector "v" can be expressed as follows:

$$v = (a, b, z).$$

Let $v_1, v_2, \ldots, v_k, \ldots v_n$ be the operation vectors indicating n operations (where n is a natural number). Let $(a_k, b_k)$ be the position in the image to be observed for $v_k$, and let $z_k$ be the scale factor in observation. Then, $v_k$ can be expressed as follows:

$$v_k = (a_k, b_k, z_k).$$

By using these expressions, the vector v" can be given as follows:

$$\hat{v} = (\hat{a}, \hat{b}, \hat{z}) \quad (1)$$

where $\hat{a} = 1/n \cdot \text{sum}(a_k)$ (k: 1 to n), $\hat{b} = 1/n \cdot \text{sum}(b_k)$ (k: 1 to n), and $\hat{z} = 1/n \cdot \text{sum}(z_k)$ (k: 1 to n).

Note that "sum($a_k$)" indicates the operation to sum the sequence of $a_k$ obtained by changing k from 1 to n.

While the present exemplary embodiment has been described with reference to the scale factor information, the scale factor information is optional. Only the observed position specified by a pathologist may be employed.

The parameter "$\Sigma$" is the covariance matrix of the above-described "v".

The parameter "$\Sigma$" can be expressed as follows:

$$\Sigma = \begin{bmatrix} Sxx & Sxy & Sxa \\ Sxy & Syy & Sya \\ Sxa & Sya & Saa \end{bmatrix} \quad (2)$$

If each of the elements of the covariance matrix in equation (2) is generalized to obtain a result Spq, Spq is expressed as follows:

$$Spq = \frac{1}{n}(p - \hat{p})^T(q - \hat{q}) = \frac{1}{n}[p_1 - p^\wedge \quad p_2 - p^\wedge \quad \cdots \quad p_n - p^\wedge] \begin{bmatrix} q_1 - q^\wedge \\ q_2 - q^\wedge \\ \cdots \\ q_n - q^\wedge \end{bmatrix} \quad (3)$$

In equation (3), p hat (p^) and q hat (q^) represent the averages of p and q, respectively. T represents transposition. Take $S_{xy}$ in the matrix $\Sigma$ in equation (2) for example, $a_1$, $a_2$, ... $a_n$ included in the operation vectors $v_1$, $v_2$, ... $v_n$ correspond to $p_1$, $p_2$, ... $p_n$ included in equation (3), respectively. In addition, $b_1$, $b_2$, $b_n$ included in the operation vectors $v_1$, $v_2$, ... $v_n$ correspond to $q_1$, $q_2$, ... $q_n$ included in equation (3), respectively. Take $S_{ya}$ in the matrix $\Sigma$ in equation (2) for example, $b_1$, $b_2$, ... $b_n$ included in the operation vectors $v_1$, $v_2$, ... $v_n$ correspond to $p_1$, $p_2$, ... $p_n$ included in equation (3), respectively. In addition, $z_1$, $z_2$, ... $z_n$ included in the operation vectors $v_1$, $v_2$, ... $v_n$ correspond to $q_1$, $q_2$, ... $q_n$ included in equation (3), respectively.

The parameter holding unit 107 prestores the parameter (v^, $\Sigma$) indicating the history of the operation.

In step S12, the next observation estimating unit 101 selects a plurality of positions as the candidates of the next position $(x^{t+1})_1$, ... $(x^{t+1})_i$, .... Note that the current position is expressed as $x^t$, which indicates that the pathologist has made t selecting operations. The position selected next time is expressed as $x^{t+1}$. The superscript (t+1) indicates the candidate of the next position selected in the (t+1)th selecting operation. For ease of understanding, the suffix i is appended to distinguish the candidates of the next position from one another. Note that in FIG. 2, the suffix i is not appended to the position $x^{t+1}$. This is only for simplicity of notation. Similarly, in the subsequent steps in FIG. 2, the suffix i is not appended. This also applies to the scale factor $(z^{t+1})_i$ described below. In this manner, each of the candidates of the next position is selected. As described below, through the processes in steps S13 to S16, the next observation estimating unit 101 selects one of a plurality of the candidates of the next position. The selected position represents the final candidate of the position that is observed by the pathologist next time.

Note that the area including the position $x^t$ differs from each of the areas including one of the candidates of the next position $x^{t+1}$. Note that all the areas are included in the captured image of the same pathological specimen. In addition, each of the positions $x^t$ and the candidates of the next position $x^{t+1}$ has a particular pixel value. That is, if one of the positions and the candidates of the next position are selected, the pixel values, which have a one-to-one correspondence with the positions, can be identified.

In step S13, the next observation estimating unit 101 reads in a pixel observation necessity level $(w(I(a, b)|(x^{t+1})_i))$ from the observation feature holding unit 106 for each of the candidates of the next position $(x^{t+1})_i$. The pixel observation necessity level is obtained in advance before the processing illustrated in FIG. 2 starts. If the position of a pixel is identified, the pixel observation necessity level corresponding to the pixel can be obtained. That is, the pixel observation necessity level $(w(I(a, b)|(x^{t+1})_i))$ can be uniquely identified for each of the candidates of the next position $(x^{t+1})_i$.

The pixel observation necessity level is a value provided for each of the pixels "I(a, b)". The degree of necessity for observing the pixel increases with increasing value (refer to FIG. 4 described below). Note that the above-described "I(a, b)" represents the pixel located at a coordinate position (a, b) in the image.

In step S14, the next observation estimating unit 101 calculates an image observation necessity level $(w((I^{t+1})_i|(x^{t+1})_i, (z^{t+1})_i))$ for each of the candidates of the next position. The image observation necessity level $(w((I^{t+1})_i|(x^{t+1})_i, (z^{t+1})_i))$ represents the degree of necessity for observing the image $(I^{t+1})$, displayed when the position $(x^{t+1})_i$ is observed with a scale factor $(z^{t+1})_i$. The image $(I^{t+1})_i$ is a partial image including the above-described position $(x^{t+1})_i$ and displayed with the scale factor $(z^{t+1})_i$. For example, an image observation necessity level can be calculated by summing the pixel observation necessity levels at all the positions in the range of an image including the above-described position $(x^{t+1})_i$ and displayed with the scale factor $(z^{t+1})_i$.

In step S15, the next observation estimating unit 101 calculates a conditional probability $(P((I^{t+1})_i, (x^{t+1})_i|x^t))$ for each of the candidates of the next position using the parameter and the image observation necessity level. The conditional probability can be obtained using equation (4) described below. Note that in equation (4), the suffix i is not appended.

In step S16, the next observation estimating unit 101 selects the candidate of the next position having the highest conditional probability and updates the information stored in the estimation result holding unit 105 by using the result of the selection as a new estimation result. Alternatively, one of the candidates may be randomly selected in accordance with the probability values. To stochastically select one of the candidates, a candidate having a high probability value is easily selected. In contrast, a candidate having a low probability value is hard to be selected. That is, even a candidate other than the candidate having the highest probability value can be selected. Such a selection method can be used when the number of operation history items collected by the pathologist is small, that is, when the parameter indicating the operation history is insufficiently calculated. The following description is given using, as an example, the case in which a candidate having the highest probability value is to be selected.

FIG. 3A illustrates an estimation result 200 held by the estimation result holding unit 105. FIG. 3B illustrates an estimation result 201 updated by the estimation result holding unit 105.

The next observation estimating unit 101 generates the estimation result 200 including at least an observation time field 202 and a coordinate field 203 and a scale factor field 204 corresponding to each of the observation times. The observation time field 202 holds the estimation results for T units of time from the current time. The minimum value of "T" is one (only one previous estimation result), and the maximum value of "T" indicates the units of time from the starting time. Note that a "unit of time" is intended to indicate the number of times. Alternatively, a "unit of time" may be a fixed or variable length of time.

After the next observation estimating unit 101 calculates a new estimation result, the estimation result holding unit 105 updates the time and holds the updated time. In addition, the estimation result holding unit 105 deletes the estimation result at the earliest time. As a result, as illustrated in FIG. 3B, the estimation result 200 is updated into the estimation result 201.

The coordinate field 203 holds the coordinates of the central point of a displayed region estimated to be observed by the pathologist. The scale factor field 204 holds the estimated display magnification. The coordinates held in the coordinate field 203 are the coordinates in a reference image held by the image pyramid holding unit 108. In addition, if the pixels of the reference image are displayed at the same magnification, the scale factor field 204 contains a value of 1.0. If the pixels of the reference image are displayed at magnification of 2×, the scale factor field 204 contains a value of 2.0. If the pixels of the reference image are displayed at magnification of 0.5×, the scale factor field 204 contains a value of 0.5.

Referring back to FIG. 2, the description will be continued.

In step S17, the displayed image generating unit 102 selects, from among a variety of image groups having different resolutions and stored in the image pyramid holding unit 108, an image of a given resolution in accordance with the selected candidate of the next position. The resolution of the selected image is the resolution identified on the basis of the scale factor "$z^{t+1}$" used in calculation of the above-described image observation necessity level. To calculate the resolution from the scale factor, a technique described in the section "Definition of Terms" is employed.

In step S18, the displayed image generating unit 102 generates an image to be displayed from the selected image. In step S19, the displayed image generating unit 102 stores the image to be displayed in the generated image holding unit 109.

Through the above-described processes, the image processing apparatus 110 can estimate the position that the pathologist who currently operates the apparatus is likely to observe next and the scale factor on the basis of a variety of pre-obtained information items regarding the operations performed by the pathologist.

The constituent element of the image display system 100 according to the present exemplary embodiment are described below.

Referring back to FIG. 1, the description will be continued. In addition, the description of each of the constituent elements is made with reference to FIG. 3A and the subsequent drawings as needed.

The next observation estimating unit 101 receives the current position and the scale factor held by the estimation result holding unit 105, the parameter held by the parameter holding unit 107, and the feature held by the observation feature holding unit 106. Thereafter, the next observation estimating unit 101 calculates the conditional probability "$p(I^{t+1}, x^{t+1}|x^t)$" as follows:

$$p(I^{t+1}, x^{t+1} | x^t) = \frac{1}{z}\exp\left(-\frac{1}{2}(u-\hat{u})^T \Sigma^{-1}(u-\hat{u})\right) w(I^{t+1} | x^{t+1}, z^{t+1}) \quad (4)$$

where $x^t$ represents an estimated position ($a^t$, $b^t$) in the image at a time of t held by the estimation result holding unit 105 (refer to FIG. 3), $x^{t+1}$ represents an estimated position vector ($a^t$, $b^t$) at the next time, Z represents the normalization factor, u is obtained as $u=v^{t+1}-v^t$, which represents a vector including a difference between the t-th position and the estimated (t+1)th position and a difference between the t-th scale factor and the estimated (t+1)th scale factor z, $v^t$ represents a vector ($a^t$, $b^t$, $x^t$) in which the estimated position ($a^t$, $b^t$) in the image at the time t and the estimated scale factor $z^t$ ("z" is a small letter) are arranged, $v^{t+1}$ represents a vector ($a^{t+1}$, $b^{t+1}$, $x^{t+1}$) in which the estimated position and the estimated scale factor at the next time are arranged. Accordingly, $u=(a^{t+1}-a^t, b^{t+1}-b^t, z^{t+1}-z^t)$. "$\hat{u}$" and "$\Sigma$" represent the average and the covariance matrix, respectively, obtained from "u" at the times t=1, 2, . . . , n. Like $\hat{v}$ in equation (1), $\hat{u}$ can be obtained by calculating the average of the values of the same element of u at the times. In addition, according to the definitions in equations (2) and (3), $\Sigma$ can be obtained by using the elements of u at each of the times.

As described above, "$\hat{v}$" and "$\Sigma$" are obtained using the pre-collected operations performed by the pathologist in advance before the processing starts and held by the parameter holding unit 107. That is, "$\hat{v}$" and "$\Sigma$" are the parameters indicating the history of operations. These values are read in in step S11 illustrated in FIG. 2. In addition, "$w(I^{t+1}|x^{t+1}, z^{t+1})$" represents the image observation necessity level for the image "$I^{t+1}$" displayed when the position "$x^{t+1}$" is observed with the scale factor "$z^{t+1}$".

Through the operation defined by equation (4), the conditional probability "$p(I^{t+1}, x^{t+1}|x^t)$" can be obtained. To obtain the image observation necessity level included in equation (4), the next image feature $I^{t+1}$, the candidate of the next position $x^{t+1}$, and the next scale factor $z^{t+1}$ are needed. The obtained conditional probability represents the probability of the next occurrence of the combination thereof. The next observation estimating unit 101 outputs the obtained conditional probability value and, in addition, the candidate of the next position $x^{t+1}$, the next scale factor $z^{t+1}$, and the next image feature $I^{t+1}$ that provide the conditional probability value.

As indicated by steps S12 to S15 of FIG. 2, the next observation estimating unit 101 calculates the conditional probability obtained using the above-described equation (4) for each of a plurality of candidates of the next position. Thereafter, the next observation estimating unit 101 selects, from among the candidates of the next position (according to the present exemplary embodiment, scale factor values are included), the candidate of the next position $x^{t+1}$ that provides the highest probability value as the estimation result.

Subsequently, the pixel observation necessity level w(I(a, b)|$x^{t+1}$) and the pixel observation necessity level required for calculating an image observation necessity level w($I^{t+1}$|$x^{t+1}$, $z^{t+1}$) are described below. Note that in the above description, the suffix i is used (e.g., ($x^{t+1}$)$_i$) to clarify that the necessity level is calculated for each of a plurality of candidates of the position. Hereinafter, the description is generalized, and the suffix i is not appended. This also applies to the drawings.

FIG. 4 illustrates a pixel observation necessity level 302 that is given for each of the coordinates and that is held by the observation feature holding unit 106. The pixel observation necessity level 302 is information that is read in from the observation feature holding unit 106 by the next observation estimating unit 101 in step S13 illustrated in FIG. 2.

The observation feature holding unit 106 holds the pixel observation necessity level 302 calculated for each of coordinates 301 of the image having a size of (W pixels)×(H pixels) using a technique described below. According to the present exemplary embodiment, the next observation estimating unit 101 calculates the image observation necessity level "$w(I^{t+1}|x^{t+1}, z^{t+1})$" using the pixel observation necessity level 302 prestored in the observation feature holding unit 106 as follows:

$$w(I^{t+1}|x^{t+1},z^{t+1})=\Sigma_{(a,b)\in D}w(I(a,b)|x^{t+1}) \quad (5)$$

where "$w(I(a, b)|x^{t+1})$" represents the pixel observation necessity level of a pixel "$I(a, b)$", "D" represents an area that is displayed on the screen when the area is observed with the scale factor of "$z^{t+1}$".

Figure 5:
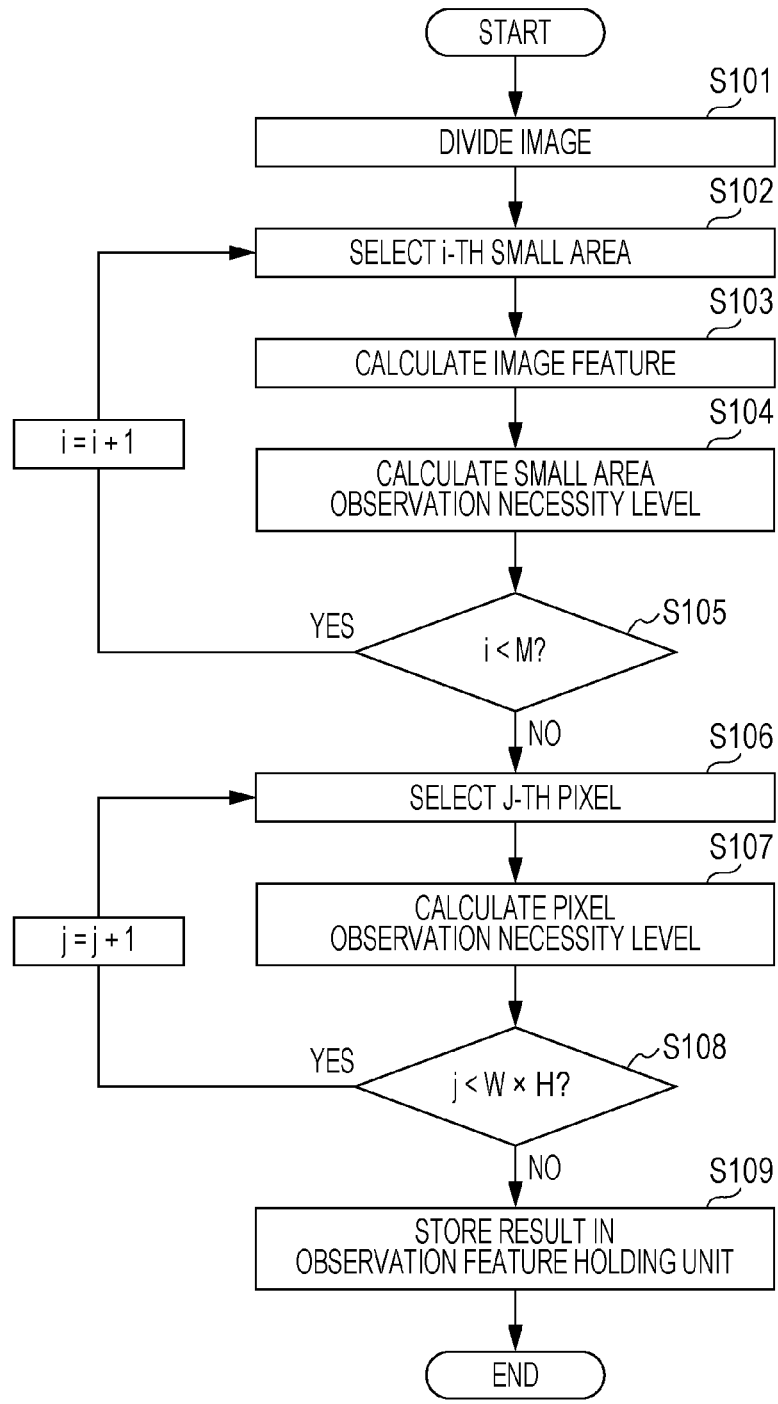
FIG. 5 is a flowchart of a technique for calculating a pixel observation necessity level.

FIG. 5 is a flowchart of a technique for calculating the pixel observation necessity level. Note that for convenience of description, the following description is given with reference to the next observation estimating unit 101 that calculates the pixel observation necessity level. However, this is only an example. The pixel observation necessity level may be calculated by a system other than the image display system 100.

The next observation estimating unit 101 calculates the pixel observation necessity level "$w(I(a, b)|x^{t+1})$" in a manner described below. In the following description, the original images are members of a set of images of a size of W pixels×H pixels.

In step S101, the next observation estimating unit 101 divides the image into M small areas "$R^i$" each having a size of (w pixels)×(h pixels) first.

Figure 6A:
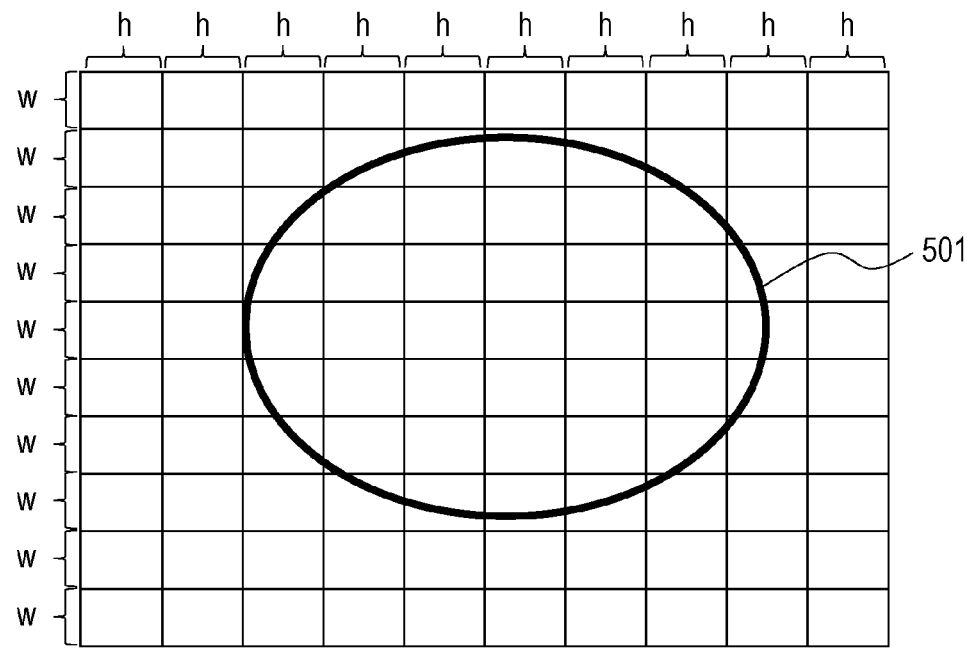
FIG. 6A is a schematic illustration of an image divided to calculate a small area observation necessity level so that any overlap is not allowed.
Figure 6B:
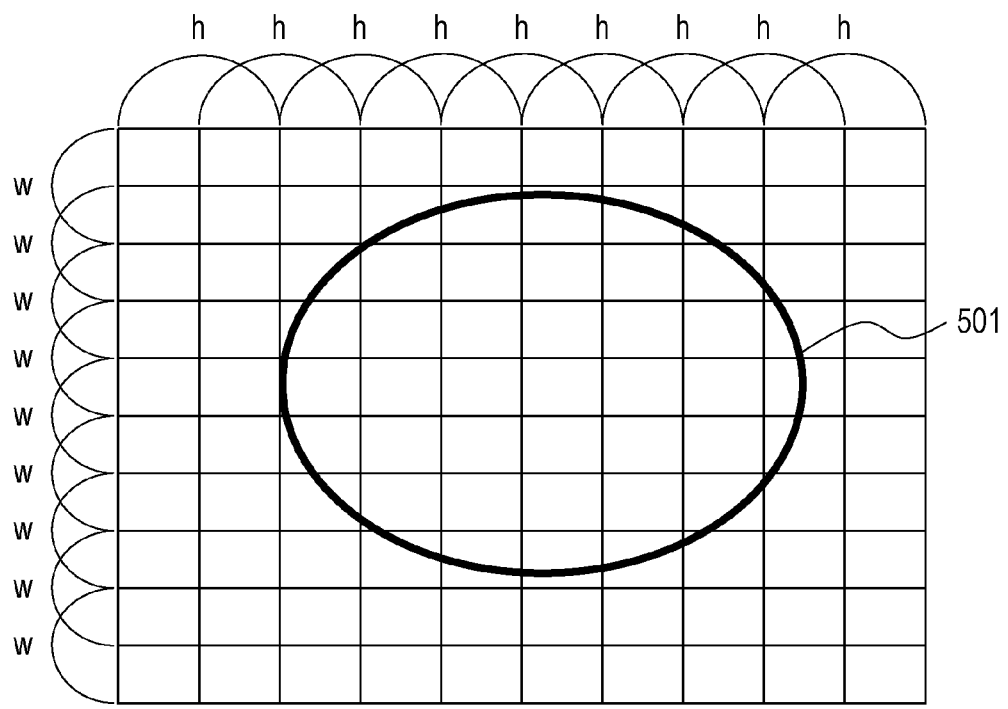
FIG. 6B is a schematic illustration of an image divided to calculate the small area observation necessity level so that overlap is allowed.

FIG. 6A illustrates an image divided into M small areas each having a size of (w pixels)×(h pixels). This image includes the captured image of a pathological specimen 501. In FIG. 6A, the small areas do not overlap one another. In contrast, FIG. 6B illustrates another example of an image divided into M small areas each having a size of (w pixels)×(h pixels). Some of the neighboring small areas overlap one another. Either one of the techniques illustrated in FIGS. 6A and 6B can be employed.

In step S102, the next observation estimating unit 101 selects the i-th small area (i=1, 2, . . . , M). In step S103, the next observation estimating unit 101 obtains the image feature of the selected small area. According to the present exemplary embodiment, as the image feature, Bag-of-features is used in order to embed the hue and the local shape of each of the regions into the image feature. The process based on the bag-of-features is described below with reference to FIG. 7.

In step S104, the next observation estimating unit 101 calculates a small area observation necessity level "$w(R^i|x^{t+1})$" from the image feature obtained in step S103. According to the present exemplary embodiment, to calculate the small area observation necessity level, support vector regression (SVR) is used. As the value of the $w(R^i|x^{t+1})$ increases, the area is more suitable region observed by the pathologist. $R^i$ represents each of the M divided small areas, and $x^{t+1}$ represents each of a plurality of candidates of the next position.

In step S105, the next observation estimating unit 101 determines whether the small area observation necessity level has been calculated for the entire region. If a small area for which the small area observation necessity level is not calculated is present (YES), i is incremented by one (i=i+1). Thereafter, the processing returns to step S102. However, if a small area for which the small area observation necessity level is not calculated is not present (NO), the processing proceeds to step S106. When the processing proceeds to step S106, the small area observation necessity level has been calculated for each of all the small areas.

In step S106, the next observation estimating unit 101 selects a pixel for which the pixel observation necessity level "$w(I(a, b)|x^{t+1})$" is to be calculated using the small area observation necessity level "$w(R^i|x^{t+1})$". At that time, the candidate of the next position $x^{t+1}$ is selected as a pixel for which the pixel observation necessity level is calculated. Note that I(a, b) represents a pixel serving as the candidate of the next position $x^{t+1}$.

In step S107, the next observation estimating unit 101 calculates the pixel observation necessity level "$w(I(a, b)|x^{t+1})$". If as illustrated in FIG. 6A, the image is divided so that the small areas do not overlap one another, the pixel observation necessity level at the j-th coordinates (a, b) is given as follows:

$$w(I(a,b)|x^{t+1})=w(R^i|x^{t+1}) \quad (6)$$

In contrast, if as illustrated in FIG. 6B, the image is divided so that the small areas overlap one another, the pixel observation necessity level at the j-th coordinates (a, b) is given as follows:

$$w(I(a,b)|x^{t+1})=\text{mean}_i(w(R^i|x^{t+1})) \quad (7)$$

where $\text{mean}_i(.)$ represents the average among the small areas each using the coordinates (a, b). Alternatively, in the overlapped areas, the largest value or the smallest value can be used.

In step S108, the next observation estimating unit 101 determines whether calculation of the pixel observation necessity level has been completed for all the pixels. If the calculation has been completed for all the pixels (NO), the processing proceeds to step S109, where the next observation estimating unit 101 stores the pixel observation necessity level in the observation feature holding unit 106. Thereafter, the processing is completed.

However, if the calculation has been not yet completed for all the pixels (YES), j is incremented by one (j=j+1). Thereafter, the processing proceeds to step S106. Subsequently, steps S106 and S107 are repeated until the calculation has been completed for all the pixels.

An example of the bag-of-features is described below with reference to FIG. 7. In bag-of-features, the local feature in the i-th small area 1501 is calculated first. As the local feature, an (r×s)-dimensional vector 1502 including local images arranged in a line is used, where each of the local images is cut out from the i-th small area 1501 and having an image size of (r pixels) by (s pixels) that is smaller than the image size (w pixels)×(h pixels). By performing the above-described process on the plurality of local images cut out from the i-th small area, a plurality of vectors are obtained from the i-th small area. At that time, since an image is generally expressed by using three colors RGB, the local feature is calculated for each of the colors. Thereafter, all the calculated local features are arranged to form a (3×r×s)-dimensional vector. In this manner, the local feature that takes into account the hue of each of the regions can be calculated. In addition, in this technique, the local image itself functions as the feature. Accordingly, the local shape in the small area is also involved as the feature. By comparing each of the local features with a representative local feature pre-calculated from the information regarding a learning image, a representative local feature that is the closest to the local feature is calculated. To calculate the representative local feature, disease images are collected for each of the types of disease, and the average of the local features calculated from the disease images can be used. Alternatively, by using all the local features generated from all the learning images (the images of the pathological specimens of a plurality of possible types), k-means clustering may be performed. Thereafter, a vector that represents the center of each of the clusters may be used as the representative local feature. Finally, the number of occurrences of the case in which each of the representative local features is determined to be the closest to each of the local features A to H calculated from the i-th small area may be counted. The numbers of counts for all the representative local features may be arranged in a line to form a vector. The vector is defined as the image feature for the i-th small area. In the case illustrated in FIG. 7, assume that eight types of representative local feature "A", "B", "C", "D", "E", "F", "G", and "H" are calculated, and a vector 1502 is the closest to "F". Then, the frequency for "F" is incremented by one. In the case where the frequency pattern for the i-th small area 1501 is set as in the frequency pattern 1503 after the above-described operation has been performed on all the local images, the image feature for the i-th small area 1501 is expressed as a vector 1504 having the values in the frequency pattern 1503 arranged therein. Since this technique does not directly use the (r×s)-dimensional vector in which the local images each having an image size of (r pixels)×(s pixels) are linearly arranged in a line, the feature that is robust to noise in the small area image can be calculated. Note that the technique for calculating the local feature is not limited to the above-described technique. For example, Scale Invariant Feature Transform (SIFT) that calculates the feature which is fixed regardless of, for example, the size of the object may be employed.

The above-described calculation of the image feature in step S103 illustrated in FIG. 5 and the above-described calculation of the observation necessity level in step S104 may be performed using a technique other than the above-described technique. For example, instead of using bag-of-features, deep-learning may be employed to learn an effective feature itself from a large amount of image data. Alternatively, instead of using SVR, random forest may be employed.

Figure 8:
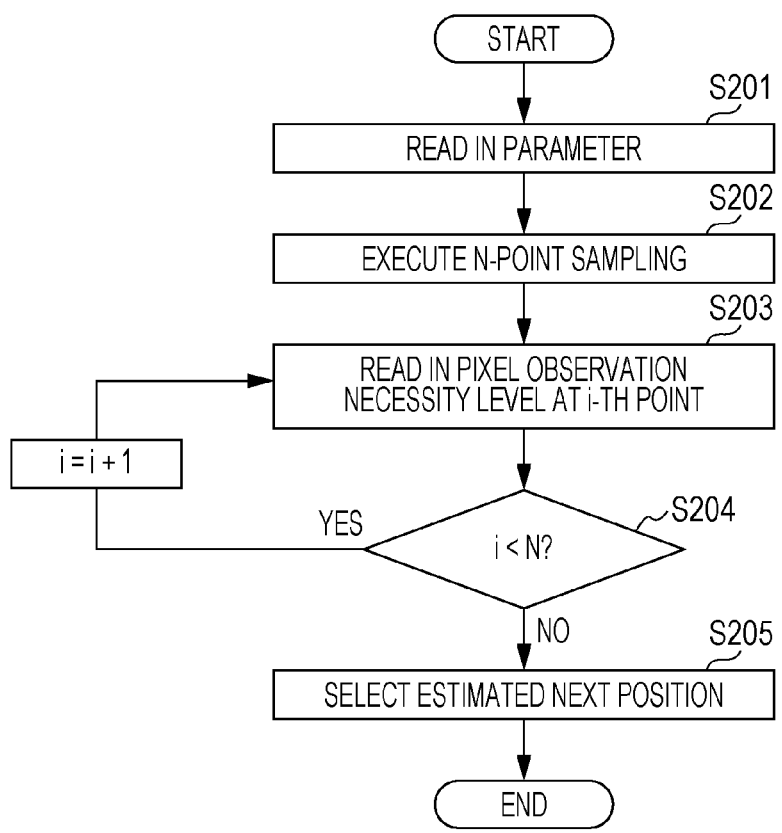
FIG. 8 is a flowchart illustrating the processing performed by a next observation estimating unit.

A calculation technique defined in equation (4) is described below with reference to a flowchart illustrated in FIG. 8. FIG. 8 is a flowchart illustrating the processing performed by the next observation estimating unit 101. The processing corresponds to the processing performed in steps S11 to S16 illustrated in FIG. 2 and is performed by the next observation estimating unit 101.

In step S201, the next observation estimating unit 101 reads in the parameters "v'" and "Σ" from the parameter holding unit 107 first. Subsequently, in step S202, the next observation estimating unit 101 executes an N-point sampling in accordance with the value of "exp(.)" in equation (4) to acquire the candidates of the next position. For the sampling, the Box-Muller method is employed. The Box-Muller method is a sampling method based on Gaussian distribution. Two values "$a_1$" and "$a_2$" in the range from −1 to +1 are randomly generated first. Subsequently, it is determined whether $a_1^2+a_2^2$ is less than or equal to 1. If $a_1^2+a_2^2$ is less than or equal to 1, "a'" is calculated as follows:

$$a' = a_i \left( \frac{-2\ln r^2}{r^2} \right)^{\frac{1}{2}} \qquad (17)$$

where "$a_i$" represents one of "$a_1$" and "$a_2$" (either one can be selected for calculation), and "$r^2$"=$a_1^2+a_2^2$. The obtained "a'" follows the Gaussian distribution of an average of 0 and a distribution of 1.

Subsequently, a random number vector α=(a', b', z') is generated using a random number that follows the Gaussian distribution of an average of 0 and a distribution of 1 generated using the above-described equation. Note that "b" and "z" are also values generated using equation (17).

Subsequently, the covariance matrix "Σ" corresponding to the inverse matrix "$\Sigma^{-1}$" in "exp(.)" in equation (4) is decomposed into a matrix "L" that satisfies $\Sigma = LL^T$. By using the matrix "L", a vector y is calculated as follows: y=v'+Lα. The obtained vector y=(a', b', z') represents a Gaussian distribution that follows an average vector "v'" and the covariance matrix "Σ". (a', b') in this vector is defined as a candidate point of the next position, and the above-described calculation is performed until N points are obtained. In this manner, N-point sampling is executed to obtain N candidate points of the next position.

As another technique, pixels located a predetermined distance from the current position in N azimuth directions may be used as the candidates of the next position. Alternatively, N candidate points of the next position may be selected by taking into account the spread of the pathological specimen in the image.

Subsequently, in step S203, the next observation estimating unit 101 reads in the pixel observation necessity level of the i-th candidate of the next position from the observation feature holding unit 106.

Subsequently, in step S204, the next observation estimating unit 101 determines whether the pixel observation necessity level has been read in for all the candidates of the next position. If a candidate of the next position for which the pixel observation necessity level has not been read in is present (YES), i is incremented by one (i=i+1). Thereafter, the processing returns to step S203. However, if the pixel observation necessity level has been read in for all the candidates of the next position (NO), the processing proceeds to step S205, where the next observation estimating unit 101 calculates the conditional probability defined in equation (4) for each of the candidates of the next position on the basis of the value of the pixel observation necessity level. In this manner, the next observation estimating unit 101 selects the final candidate of the next position from among the candidates of the next position.

Figure 9:
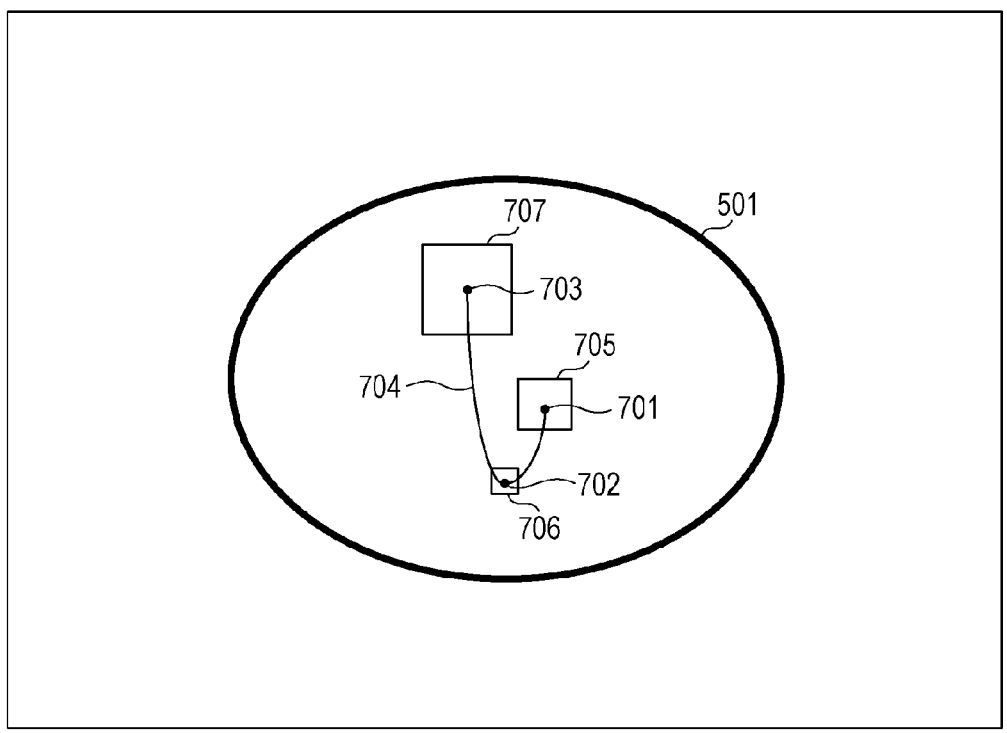
FIG. 9 illustrates non-linear estimation performed on an image as a result of estimation of the next position.

According to the present exemplary embodiment, the next observation estimating unit 101 selects, as the final candidate of the next position, the position at which the conditional probability obtained through the calculation of equation (4) is the highest. For example, FIG. 9 illustrates the sequentially obtained results of estimation of the next position 701, 702, and 703. As can be seen from FIG. 9, if the results of estimation of the next position 701, 702, and 703 are connected using a line 704, the movement of the estimated next position is non-linear in the entire image.

In addition, square frames 705, 706, and 707 in FIG. 9 represent displayed screen areas at each time. The displayed screen area varies in accordance with the scale factor. A narrower area of the image is displayed with increasing scale factor. When the square frames 705, 706, and 707 are actually displayed, the image having a resolution corresponding to the scale factor is selected from among the images in the image pyramid holding unit 108.

Immediately after the pathologist starts observation, the displayed image generating unit 102 reads in, from the image pyramid holding unit 108, low-resolution image data including the entire image as the initial information and stores the image data in the generated image holding unit 109. Subsequently, the displayed image generating unit 102 reads in, from the image pyramid holding unit 108, an image corresponding to the target position and having the resolution corresponding to the target scale factor in accordance with the estimated next position and the estimated next scale factor output from the next observation estimating unit 101.

As described above, the displayed screen area is related to the scale factor. As the image needs to be observed in more detail, the scale factor becomes higher and the displayed area of the pathological specimen becomes narrower. According to the present exemplary embodiment, upon displaying an image with a high scale factor, the displayed image generating unit 102 reads in the high-resolution image data stored in the image pyramid holding unit 108. In contrast, upon displaying an image with a low scale factor, the displayed image generating unit 102 reads in the low-resolution image data stored in the image pyramid holding unit 108. Thereafter, the displayed image generating unit 102 cuts out an area required for display from the read-in image on the basis of the estimated position and outputs the cutout image to the generated image holding unit 109 as an image to be displayed.

Figure 10A:
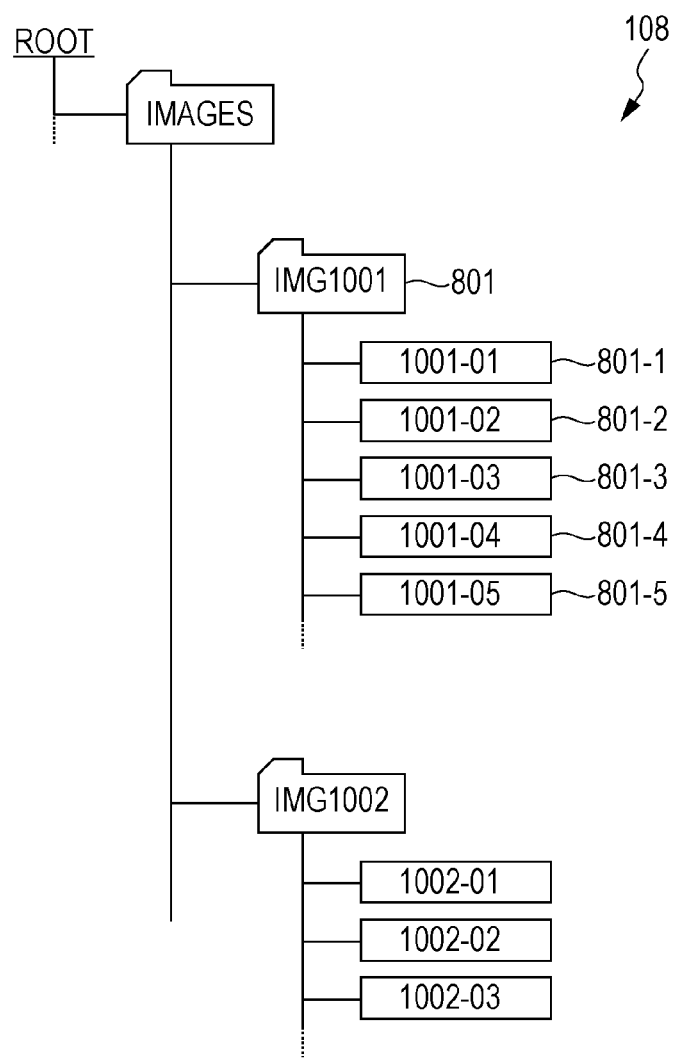
FIG. 10A is a schematic illustration of the data structure in an image pyramid holding unit.

FIG. 10A illustrates an example of the storage structure of the image data file in the image pyramid holding unit 108. In the image pyramid holding unit 108, an image folder ("IMAGES") is provided as a root folder ("ROOT"). Immediately below the image folder, sub-folders ("IMG1001" and "IMG1002") are further provided. The sub-folder may be provided on an examinee basis or on a pathological specimen basis.

Each of the sub-folders stores an image data file (an image file). For example, five image files 801-1 to 801-5 are stored in a sub-folder 801. The image files 801-1 to 801-5 are, for example, the images obtained by capturing the image of the same pathological specimen with different resolutions.

According to the present exemplary embodiment, since a plurality of images having resolutions that sequentially increase or decrease are provided like a pyramid, the images are also referred to as an "image pyramid".

Figure 10B:
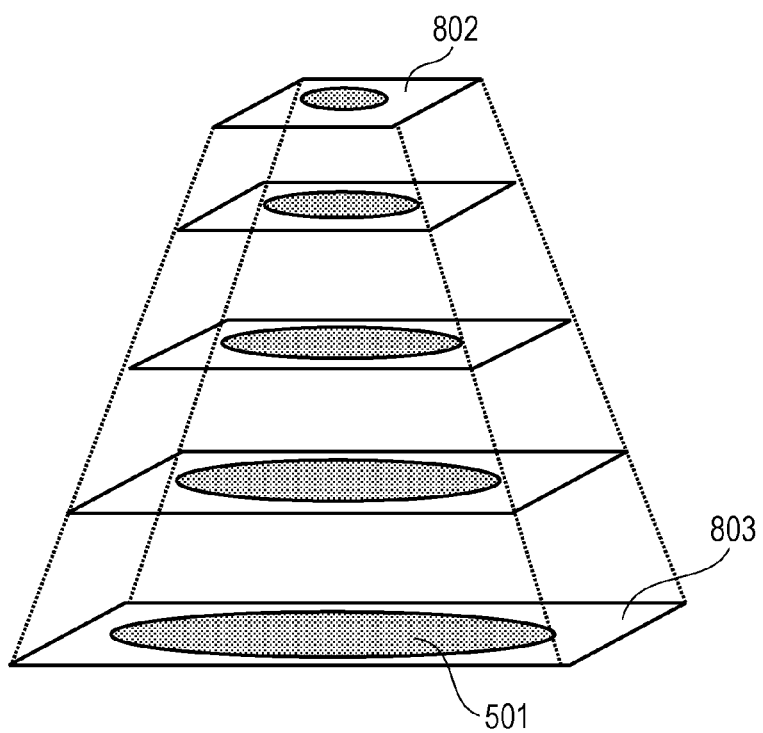
FIG. 10B illustrates the concept of an image pyramid in the image pyramid holding unit 108.

FIG. 10B illustrates the concept of the image pyramid. Each of the images includes the same pathological specimen 501. The image size (the resolution) of the topmost image 802 is the smallest, and the image of the bottommost image 803 is the largest. By holding the image files having different resolutions, the need for an image enlargement process and an image reduction process can be eliminated. Accordingly, the speed of generation of an image to be displayed (described below) can be increased.

The image display unit 103 is formed as a widely used display. The image display unit 103 presents the image stored in the generated image holding unit 109 to the pathologist. The image is generated by the displayed image generating unit 102 in accordance with the information input by the pathologist via the input unit 104 (described in more detail below).

The input unit 104 receives, from the user (the pathologist), an instruction to operate the image display system 100. The input unit 104 has a mechanism that allows the pathologist to input the position and the scale factor. The input unit 104 outputs the input information to the image display unit 103. In addition, if the position and the scale factor that differ from the estimation result estimated by the next observation estimating unit 101 are input, the input unit 104 outputs, to the next observation estimating unit 101, an instruction to temporarily stop the estimation. Upon receiving the instruction, the next observation estimating unit 101 changes the current position and scale factor to the values input by the pathologist and restarts the next observation estimation. Thereafter, the next observation estimating unit 101 stores the input values and the output values in the estimation result holding unit 105.

According to the present exemplary embodiment, the image processing apparatus can automatically estimate the next position to be observed by the pathologist and the next scale factor in accordance with the image feature and present the image to the pathologist. Accordingly, a medical technologist need not be present while the pathologist observes a specimen. In addition, estimation of the next position can be corrected in accordance with the input information input to the input unit 104 as needed.

The operations performed by the next observation estimating unit 101 and the observation feature holding unit 106 are not limited to those of the present exemplary embodiment. For example, exp(.) in equation (4) may be replaced with an arithmetic operation using, for example, mixture gaussian distribution, t distribution, or beta distribution. In such a case, in step S12 illustrated in FIG. 2, instead of making selection based on the conditional probability, a plurality of candidates of the position and scale factors are sampled first. Thereafter, the candidate of the next position is selected on the basis of the probability values calculated from the plurality of candidates. Alternatively, the observation feature holding unit 106 may determine only whether the current position is within the specimen. In addition, the next observation estimating unit 101 may instruct the pathologist to input the direction of movement using the input unit 104 and pre-read the image in the desired direction at a constant speed with the scale factor fixed. In addition, when the pathologist performs an enlargement or reduction operation, the next observation estimating unit 101 may change the scale factor in the desired direction with the position fixed.

Figure 11A:
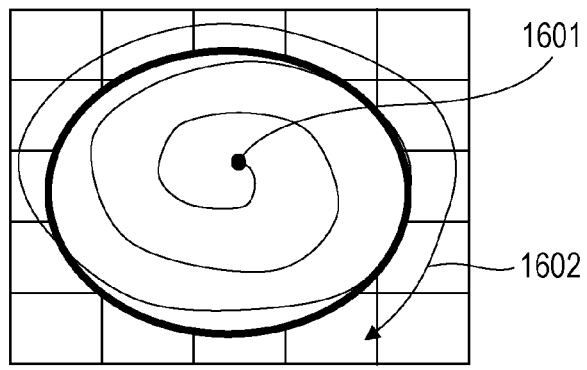
FIG. 11A illustrates a pre-read operation in accordance with certain movement.
Figure 11B:
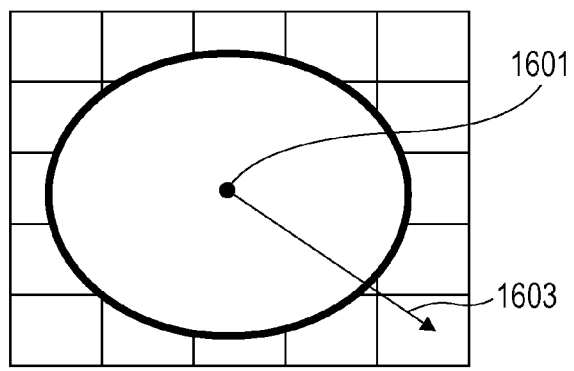
FIG. 11B illustrates a pre-read operation in accordance with certain movement.
Figure 11C:
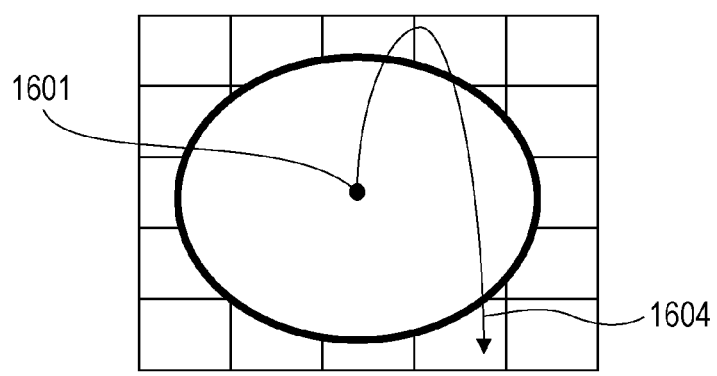
FIG. 11C illustrates a pre-read operation in accordance with certain movement.

FIGS. 11A to 11O illustrate a pre-read operation in accordance with certain movement. As illustrated in FIGS. 11A to 11O, the image may be pre-read in accordance with certain movement starting from a position 1601 specified by the pathologist. For example, as illustrated in FIG. 11A, the image may be pre-read in a spiral form 1602 that starts from the position 1601 specified by the pathologist. Alternatively, as illustrated in FIG. 11B, the image may be pre-read along a straight line 1603. Still alternatively, as illustrated in FIG. 11C, the image may be pre-read along an N-order function curve 1604 (N=2, 3, . . . ). Yet still alternatively, the image may be pre-read along a curve formed as a combination of the above-described curves. For example, only when the observation feature holding unit 106 determines that the position is within the specimen, the processing of the next observation estimating unit 101 may be performed.

Second Exemplary Embodiment

Unlike the image display system according to the first exemplary embodiment, an image display system according to the present exemplary embodiment includes a super-resolution processing unit. Thus, an image having a resolution that is higher than the highest resolution of the image stored in the image pyramid holding unit 108 can be presented to the pathologist.

Figure 12:
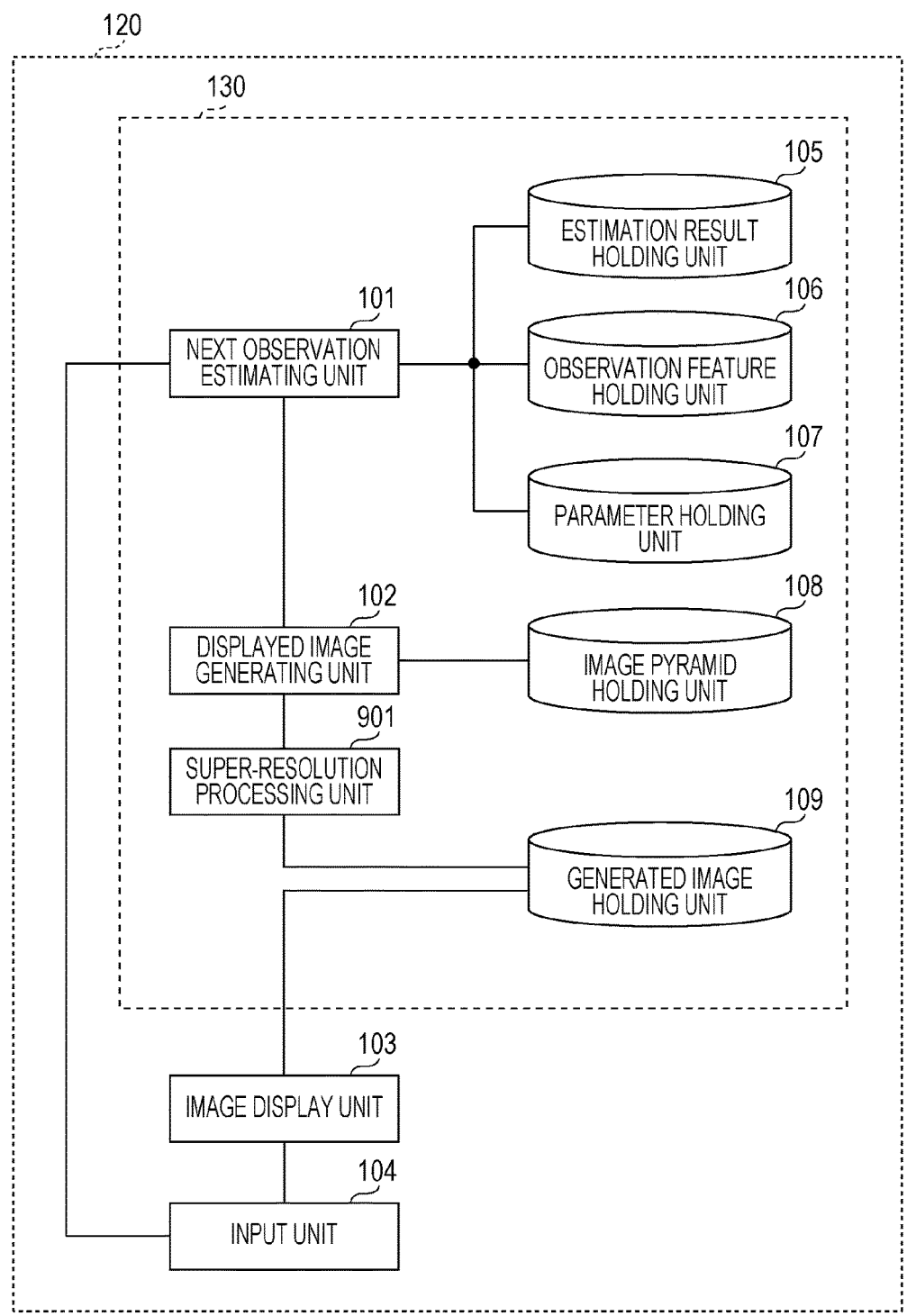
FIG. 12 is a block diagram of the configuration of an image display unit according to a second exemplary embodiment.

FIG. 12 is a block diagram of an image display system 120 according to the present exemplary embodiment. The image display system 120 includes an image processing apparatus 130, an image display unit 103, and the input unit 104. The image processing apparatus 130 is similar to the image processing apparatus 110 (refer to FIG. 1) except for including the super-resolution processing unit 901. The present exemplary embodiment is described below with reference to FIG. 12. Note that the same numbering will be used in describing a constituent element in FIG. 12 as was utilized above in describing FIG. 1, and detailed description of the constituent element is not repeated.

In the first exemplary embodiment, the displayed image generating unit 102 generates an image to be presented to the pathologist in accordance with the estimation result of the next observation estimating unit 101. At that time, if the estimated scale factor is a value that cannot be obtained without magnifying the image 803 having the highest resolution (refer to FIG. 10B), the image can be magnified using an image interpolation process, such as linear interpolation or spline interpolation. In this manner, the scale factor can be increased. However, the resolution cannot be increased. Accordingly, although the pathologist observes the image after increasing the scale factor, it is difficult for the pathologist to recognize the detailed shape of the pathological specimen. To address such an issue, according to the present exemplary embodiment, a super-resolution process is performed using the super-resolution processing unit 901.

The super-resolution process is one of image processing techniques for improving the resolution. An example of the super-resolution process is described below. A plurality of images of a pathological specimen are captured while lighting the pathological specimen from different directions. These images are automatically combined into a magnified image having pixels equal in number to the total number of pixels of the plurality of images (i.e., a patchwork image is generated). Since the magnified image is formed by simply combining the plurality of images, the image is not a high-resolution image. Thereafter, deconvolution is performed on a small area of the magnified image corresponding to a predetermined partial area to obtain a high-resolution image. In this manner, the super-resolution process is performed.

According to the present exemplary embodiment, a deconvolution process is performed in order to remove the influence of the point spread function (PSF) based on a variation of, for example, the lens used for image capturing, the thickness of the pathological specimen, and the amount of an encapsulating medium.

As used herein, the term "deconvolution process" refers to an inverse transformation process defined by the following equation:

$$\hat{I} = D^{-1} * I \tag{8}$$

where "*" represents the convolution operation, "$\hat{I}$" represents the high-resolution image to be obtained, "I" represents the image 803 having the highest resolution and stored in the image pyramid holding unit 108, and "D" represents a filter corresponding to PSF used in deconvolution. According to the present exemplary embodiment, the value of "D" is set using a Gaussian filter expressed as follows:

$$D(a, b) = \frac{1}{2\pi\sigma^2} \exp\left(-\frac{a^2 + b^2}{2\sigma^2}\right) \tag{9}$$

where "$\sigma^2$" represents a parameter indicating the variance, and "D(a, b)" represents the filter value at row a and column b. Note that the filter "D" can be set to any value as follows:

$$D = D_g * (W + \Delta) \tag{10}$$

where "$D_g$" represents a Gaussian filter as in equation (9), "W" is a value determined on the basis of the aperture ratio of the imaging element and the resolution increase ratio, and "$\Delta$" represents a deviation between an actual value and a setting value. For example, when the resolution is increased to three times the original resolution using an imaging element having a aperture ratio of 25%, "W" can be set as follows:

$$W = \frac{1}{4}\begin{pmatrix} 1/4 & 1/2 & 1/4 \\ 1/2 & 1 & 1/2 \\ 1/4 & 1/2 & 1/4 \end{pmatrix} \tag{11}$$

Note that the values of "$\Delta$" is set using, for example, a random value or white noise.

According to the present exemplary embodiment, to obtain "$\hat{I}$" defined in equation (8), an operation in the frequency domain using a Wiener filter is performed as follows:

$$H(\hat{I}) = H(D)^{-1} H(I) \tag{12}$$

where "H(.)" represents transformation into the frequency domain, and "$H(D)^{-1}$" is given as follows:

$$H(D)^{-1} = \frac{H(D)}{H(D)^2 + \Gamma} \tag{13}$$

where "$\Gamma$" is a parameter indicating the S/N ratio. According to the present exemplary embodiment, as the deconvolution process, the operation in the frequency domain using the Wiener filter is employed. However, the above-described process is only an example. The deconvolution process is not limited thereto. Any appropriate process can be employed. For example, the deconvolution process may be performed using the following update equation:

$$I_{a,b}^{r+1} = I_{a,b}^r - \rho \frac{\partial E}{\partial I_{a,b}} \tag{14}$$

where "$I_{a,b}^{r+1}$" represents the pixel value at the coordinates (a, b) in the r-th repetitive operation, "$\rho$" represents the parameter at the time of update, "E" represents the following error function:

$$E = (I - D * \hat{I})^2 \tag{15}$$

Equation (14) can be obtained by differentiating equation (15) with respect to "$I_{a,b}$". Alternatively, when noise in the image is taken into account, the update equation obtained by differentiating an equation obtained by adding L2 norm and L1 norm to equation (15) can be employed.

Figure 13:
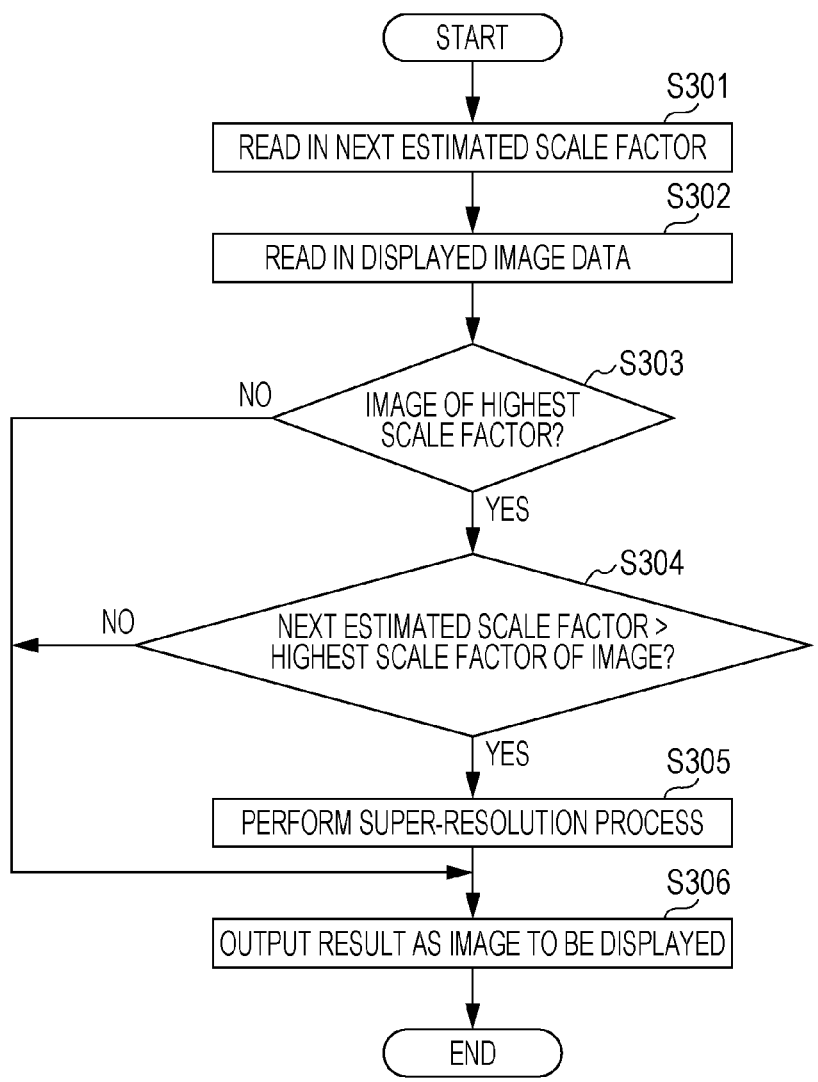
FIG. 13 is a flowchart indicating the processing performed by a super-resolution processing unit.

FIG. 13 is a flowchart indicating the processing performed by the super-resolution processing unit 901.

In step S301, the super-resolution processing unit 901 reads in the estimated next scale factor, which is the output information of the next observation estimating unit 101 first. Subsequently, in step S302, the super-resolution processing unit 901 reads in the data of the image to be displayed output from the displayed image generating unit 102. Subsequently, in step S303, the super-resolution processing unit 901 determines whether the read-in image is the image 803 having the highest resolution. If the read-in image is the image 803 having the highest resolution (YES), the processing proceeds to step S304.

However, if the read-in image is not the image 803 (NO), the processing proceeds to step S306, where the super-resolution processing unit 901 outputs, to the image display unit 103, the image 803 having the highest resolution as the image to be displayed.

Subsequently, in step S304, the super-resolution processing unit 901 determines whether the super-resolution process is necessary. If the estimated next scale factor is higher than that of the image 803 having the highest resolution (YES), the processing proceeds to step S305, where the super-resolution processing unit 901 performs the super-resolution process. However, if the estimated next scale factor is lower than that of the image 803 having the highest resolution (NO), the processing proceeds to step S306, where the super-resolution processing unit 901 outputs the result of the super-resolution process to the image display unit 103 as the image to be displayed.

According to the present exemplary embodiment, an image having a resolution that is higher than the resolution of the image stored in the image pyramid holding unit 108 can be presented to the pathologist. Accordingly, the need for re-acquisition of the images to obtain a higher-resolution image can be eliminated.

Third Exemplary Embodiment

Unlike the image display systems according to the first and second exemplary embodiments, an image display system according to the third exemplary embodiment includes a result display control unit and a magnifying operation determination unit. The result display control unit performs control to display the indication of the estimated position and scale factor in the displayed entire image and the information as to whether the super-resolution process has been performed. The magnifying operation determination unit determines whether a predetermined number or more of successive magnifying operations have been performed on the input unit. If the predetermined number or more of successive magnifying operations have been performed, the super-resolution process is performed on the area. According to such a configuration, the pathologist can visually recognize which area of the image can be displayed, with which scale factor the area can be displayed, and which region has been subjected to the super-resolution process. In addition, if an area that is not estimated to be the next position is selected using the result display control unit, the estimation of the next position can be restarted from the selected area. Furthermore, since the configuration includes the magnifying operation determination unit, the super-resolution process can be performed even when the super-resolution processing unit determines that the super-resolution process is not needed.

Figure 14:
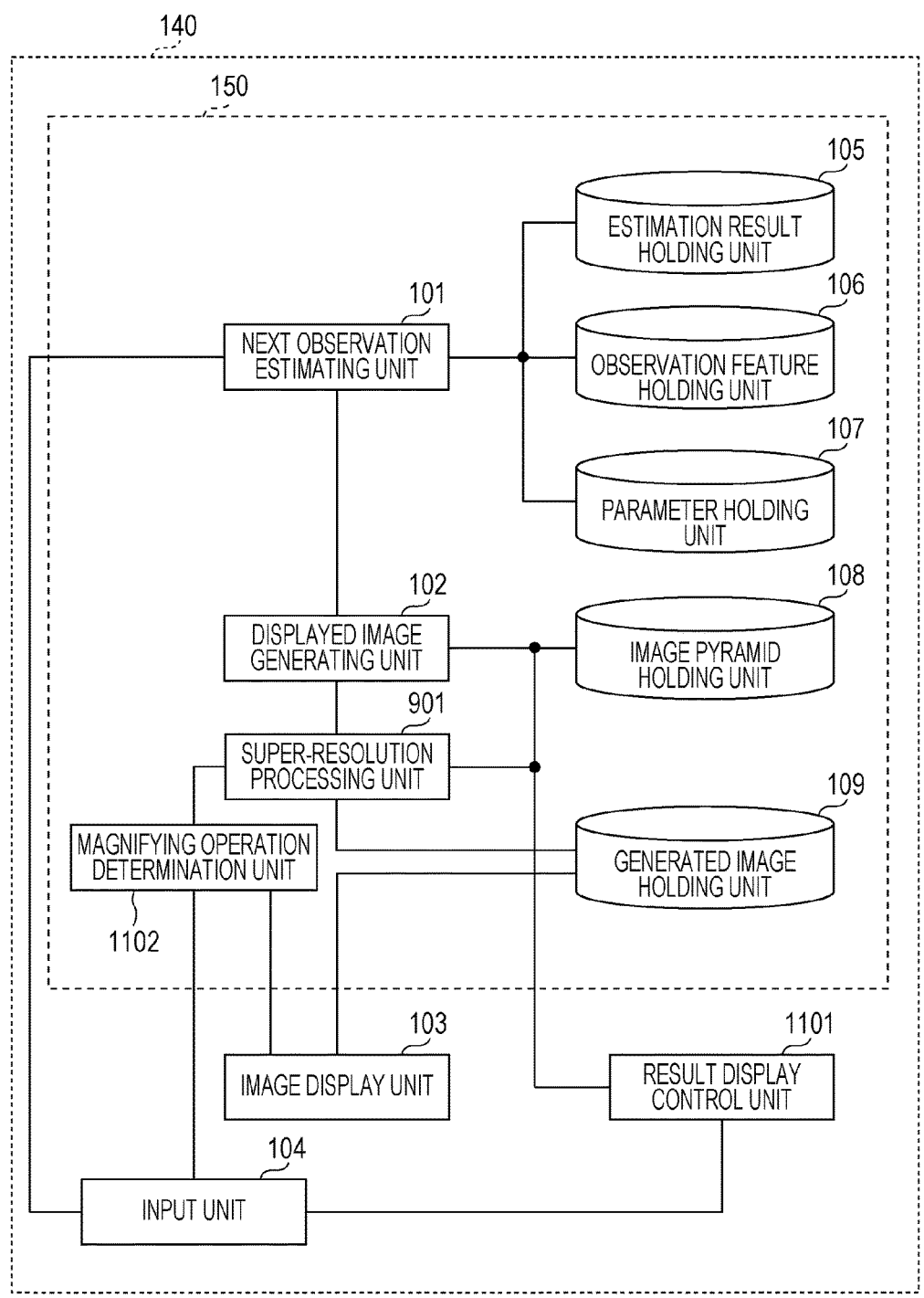
FIG. 14 is a block diagram of an image display system according to a third exemplary embodiment.

FIG. 14 is a block diagram of an image display system 140 according to the present exemplary embodiment. The image display system 140 includes an image processing apparatus 150, an image display unit 103, an input unit 104, and a result display control unit 1101. The image processing apparatus 150 is similar to the image processing apparatus 130 (refer to FIG. 12) except for including a magnifying operation determination unit 1102. The present exemplary embodiment is described below with reference to FIG. 14. Note that the same numbering will be used in describing a constituent element in FIG. 14 as was utilized above in describing FIG. 1, and detailed description of the constituent element is not repeated.

The result display control unit 1101 receives the output information output from the super-resolution processing unit 901 and the output information output from the next observation estimating unit 101. Thereafter, the result display control unit 1101 performs control to display the bird's-eye view of the entire image showing which part is estimated to be the next position by the next observation estimating unit 101 and which part has been subjected to the super-resolution process.

In addition, if some region displayed on the image display unit 103 is specified by the pathologist using the input unit 104, the result display control unit 1101 displays an input tab used to input the display magnification. Thereafter, the result display control unit 1101 prompts the pathologist to input the display magnification via the input unit 104. In addition, the result display control unit 1101 sends, to the displayed image generating unit 102, the information regarding the region (the area) specified by the pathologist via the input unit 104.

If the scale factor and/or the area is specified via the input unit 104, the input unit 104 outputs, to the next observation estimating unit 101, an instruction to temporarily stop the estimation. Upon receiving the instruction, the next observation estimating unit 101 temporarily stops the estimation. Thereafter, the next observation estimating unit 101 updates the current position and the scale factor to the values input by the pathologist and newly starts estimation of the next observed point. The next observation estimating unit 101 stores the input values and the output values in the estimation result holding unit 105.

Figure 15A:
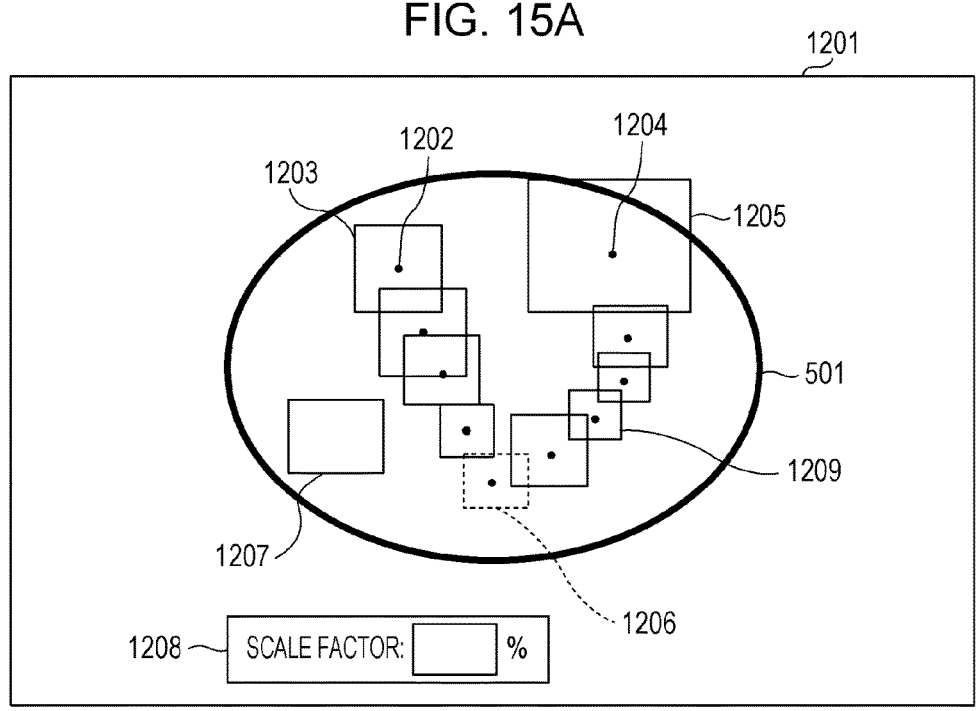
FIG. 15A is a schematic illustration of a display example displayed by a result display control unit.

FIG. 15A illustrates a display example 1201 controlled by the result display control unit 1101. In FIG. 15A, estimation starts at a position 1202 and the display area 1203, and a plurality of estimation processes are performed along the shape of U. Finally, the estimation is completed at a position 1204 and a display area 1205.

A display area 1206 shown as a dotted line indicates a region subjected to the super-resolution process. At that time, the pathologist selects a display area 1207 using the input unit 104. The result display control unit 1101 displays a tab 1208 used to input the display magnification. The pathologist inputs, using the input unit 104, the scale factor with which he or she wants to display the display area 1207. Thereafter, the super-resolution processing unit 901 determines whether the performance of the super-resolution process is needed using the information input to the tab 1208. If the performance of the super-resolution process is needed, the super-resolution process is performed. However, if the performance of the super-resolution process is not needed, the displayed image generating unit 102 selects an image having a different resolution and displays the selected image.

If a predetermined number or more of successive zoom-in operations have been performed on the image display unit 103 via the input unit 104 and if the super-resolution process has never been performed, the magnifying operation determination unit 1102 outputs, to the super-resolution processing unit 901, an instruction to perform the super-resolution process on the displayed image.

Note that the input unit 104 can be integrated with the image display unit 103 to form a touch screen panel display. If the pathologist touches part of an image indicating the pathological specimen displayed on the display with two fingertips and performs a predetermined number or more of pinch-out operations within a predetermined period of time, the magnifying operation determination unit 1102 outputs, to the super-resolution processing unit 901, an instruction to perform the super-resolution process on the part of the image.

Figure 15B:
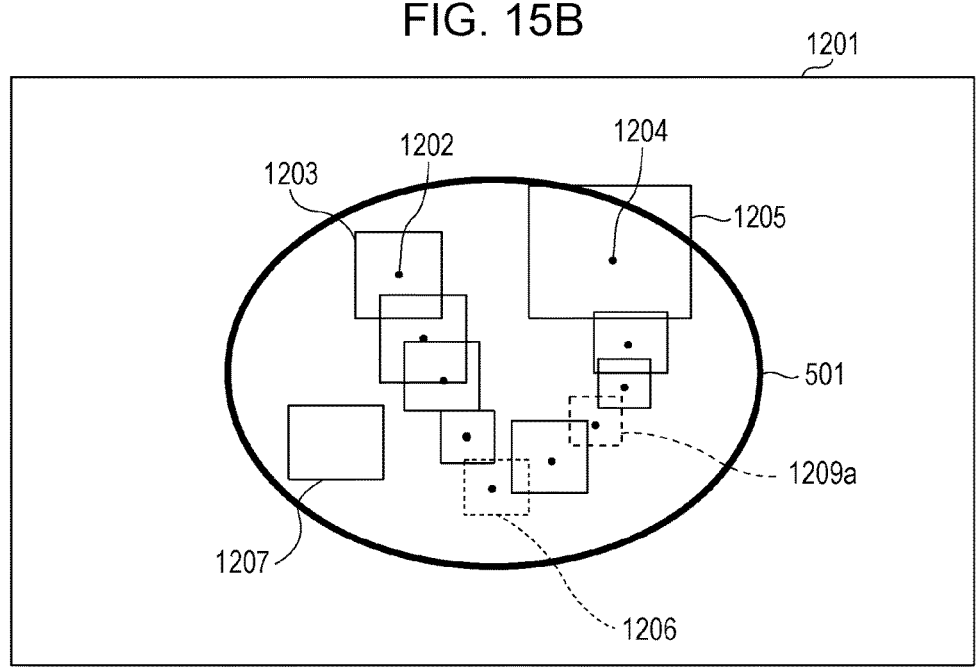
FIG. 15B is a schematic illustration of a display example displayed by the result display control unit when an area not subjected to a super-resolution process is subjected to the super-resolution process in accordance with information input via an input unit.

An example of the display control operation performed by the result display control unit 1101 is described below with reference to FIGS. 15A and 15B. When observing a display area 1209 that is not subjected to the super-resolution process, the pathologist performs a predetermined number or more of successive zoom-in operations. At that time, the super-resolution process is performed on the display area 1209. FIG. 15B illustrates a portion 1209a of the image subjected to the super-resolution process.

According to the present exemplary embodiment, the pathologist can visually recognize which region in the image can be displayed, with which scale factor the region can be displayed, and which region has been subjected to the super-resolution process. In addition, by selecting, on the result display control unit 1101, an area that is not estimated to be the next position by the next observation estimating unit 101, the estimation of the next position can be newly started from the selected area. Furthermore, by providing the function for allowing the pathologist to input the scale factor after selecting the area or the magnifying operation determination unit 1102, the super-resolution process can be performed even when the super-resolution processing unit 901 determines that the super-resolution process is not needed.

While the image display systems have been described with reference to the exemplary embodiments of the present disclosure, the present disclosure is not limited to the exemplary embodiments. Modifications of the exemplary embodiments are described below.

MODIFICATIONS

According to the above-described first exemplary embodiment, "$v^t$" included in "$u$" defined by equation (4) is a vector including the estimated position and the pathological specimen which are arranged elements. However, the elements of the vector are only example.

For example, "$v^t$" may further include the image feature. In the case of employing "$u$" defined using a vector "$v^t$" including the estimated position in the image at a time t, the image feature, and the estimated scale factor that are arranged, the probability distribution is given as follows:

$$p(I^{t+1}, x^{t+1} | x^t) = \frac{1}{z}\exp\left(-\frac{1}{2}(u-\hat{u})^T \Sigma^{-1}(u-\hat{u})\right) \quad (16)$$

$v^t$=[the coordinates, the image feature, the scale factor]$^T$. For example, $v^t$ can be expressed as follows:

$$v^t = [a^t, b^t, f^t, z^t]^T$$

where the superscript "t" of $v^t$ represents the t-th selected position. At that time, the coordinates of the pixel is written as ($a^t$, $b^t$), the image feature is written as $f^t$, and the scale factor is written as $z^t$.

Since the image feature $f^t$ is included in $v^t$, the image feature needs to be extracted for each of the observed positions in addition to the scale factor. For example, for each of the pixels of the image of the pathological specimen or each of the areas including a plurality of pixels (the region of the pathological specimen) of the image, an observation level indicating whether the operator needs to observe the pixel or the area is assigned to the pixel or the area. Thereafter, the observation level can be used as the image feature. For example, the observation level is defined by a plurality of states obtained by dividing the range from the state in which the observation is needed to the state in which the observation is not needed. The level from the level that requires observation to the level that does not require observation may be represented by a gradually changing color, and the information regarding an image including the variation of the color may be held as the information indicating the image feature. For example, the number of the observation levels in the range from the state in which the observation is needed to the state in which the observation is not needed is set to five. The saturation of the color that is available for the image of the pathological specimen is divided into five, that is, C1 to C5 in the order of lowest to highest saturation. If the image having C5, which is the highest saturation, is included, the tissue appearing in the image is at an observation level that requires observation. However, if the image having C1, which is the lowest saturation, is included, the tissue appearing in the image is at an observation level that does not require observation. By employing the saturation as the image feature $f^t$, the saturation can be used as an element used to calibrate the above-described $v^t$.

By using the image feature as an element of the vector v in addition to the coordinates and the scale factor, the covariance matrix becomes a 4×4 matrix. Since this is apparent to a person skilled in the art, the detailed description is not provided.

When equation (16) is employed, an element of the image feature is included in "$v^t$" used for the definition of "$u$" and "$\hat{u}$". Accordingly, the image observation necessity level "$w(I^{t+1}|x^{t+1}, z^{t+1})$" in equation (4) is not needed. That is, the conditional probability can be obtained by using Gaussian (the Gauss function) appearing in the right-hand side of equation (16). Note that in equation (16), instead of the Gauss function, the mixture gaussian distribution or the t distribution, for example, can be employed. In such a case, instead of selecting a candidate of the next position on the basis of the conditional probability obtained using equation (16), the candidate of the next position is selected on the basis of the values obtained by sampling a plurality of candidates first and, thereafter, calculating the probability value of each of the candidates of the position.

The next observation estimating unit 101 receives the current estimated position and the scale factor held by the estimation result holding unit 105 and the parameter held by the parameter holding unit 107 and calculates the conditional probability "$p(I^{t+1}, x^{t+1}|x^t)$" defined in equation (16). Thereafter, the next observation estimating unit 101 outputs the next position, the next scale factor, and the next image feature on the basis of the result of calculation.

As a further modification, regardless of the information about the scale factor and the image feature, $v^t$ including only the coordinates can be used in equations (4) and (16). That is, $v^t$=[the coordinates]. Note that $v^t$ can be a two-dimensional vector. However, by using a vector $v^t$ in which the value of an unwanted element (e.g., the scale factor) other than the position is set to "0", equation (16) can be used without any change.

When the conditional probability is calculated using $v^t$ including only the information regarding the position, the processing illustrated in FIG. 2 can be simplified.

Figure 16:
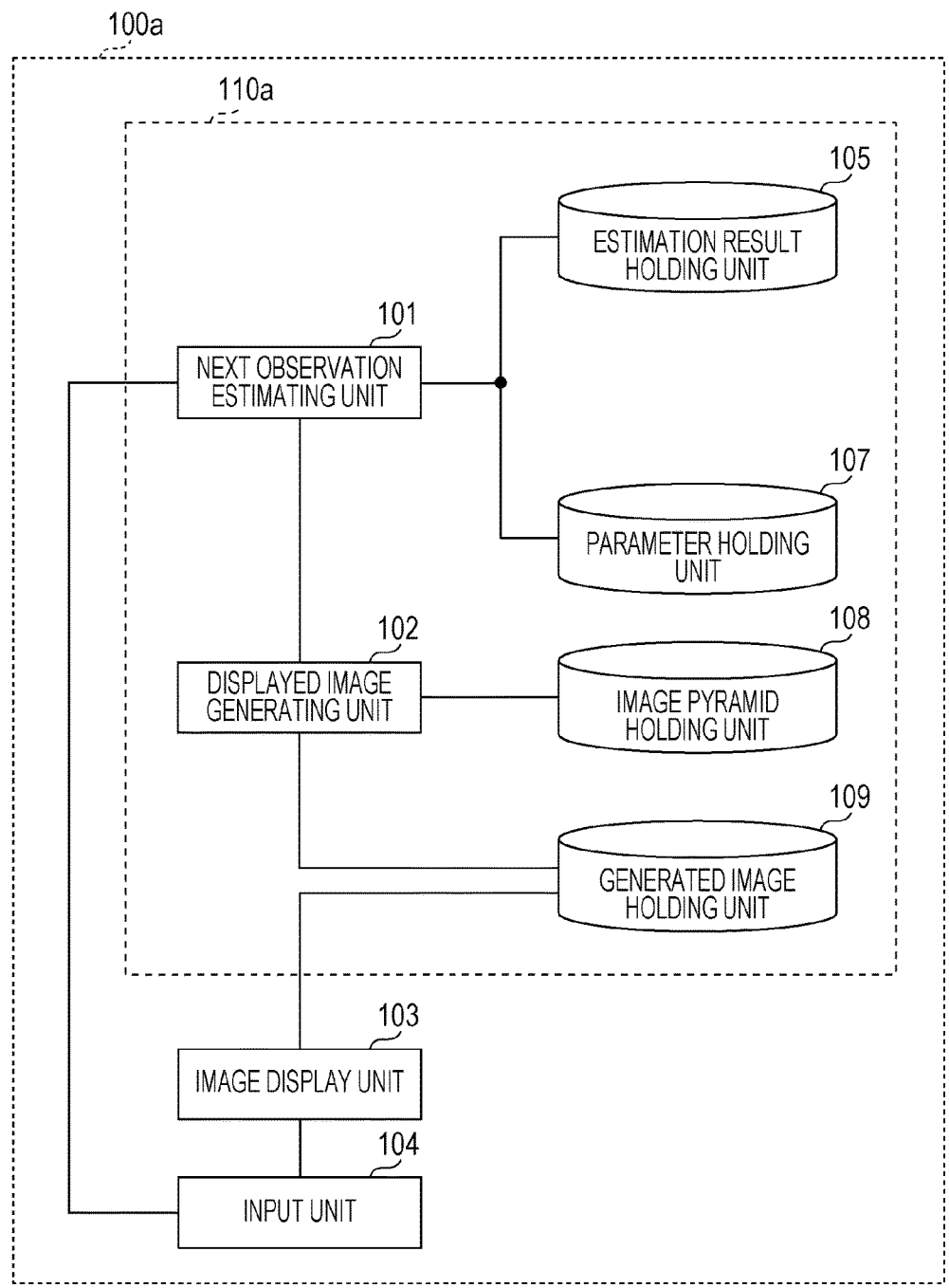
FIG. 16 illustrates an example of the configurations of an image display system including an image processing apparatus not including an observation feature holding unit.

FIG. 16 illustrates an example of the configurations of an image display system 100a and an image processing apparatus 110a that calculate the conditional probability using $v^t$ including only the information regarding the position. Unlike the image processing apparatus 110 illustrated in FIG. 1, the image processing apparatus 110a does not include the observation feature holding unit 106.

Figure 17:
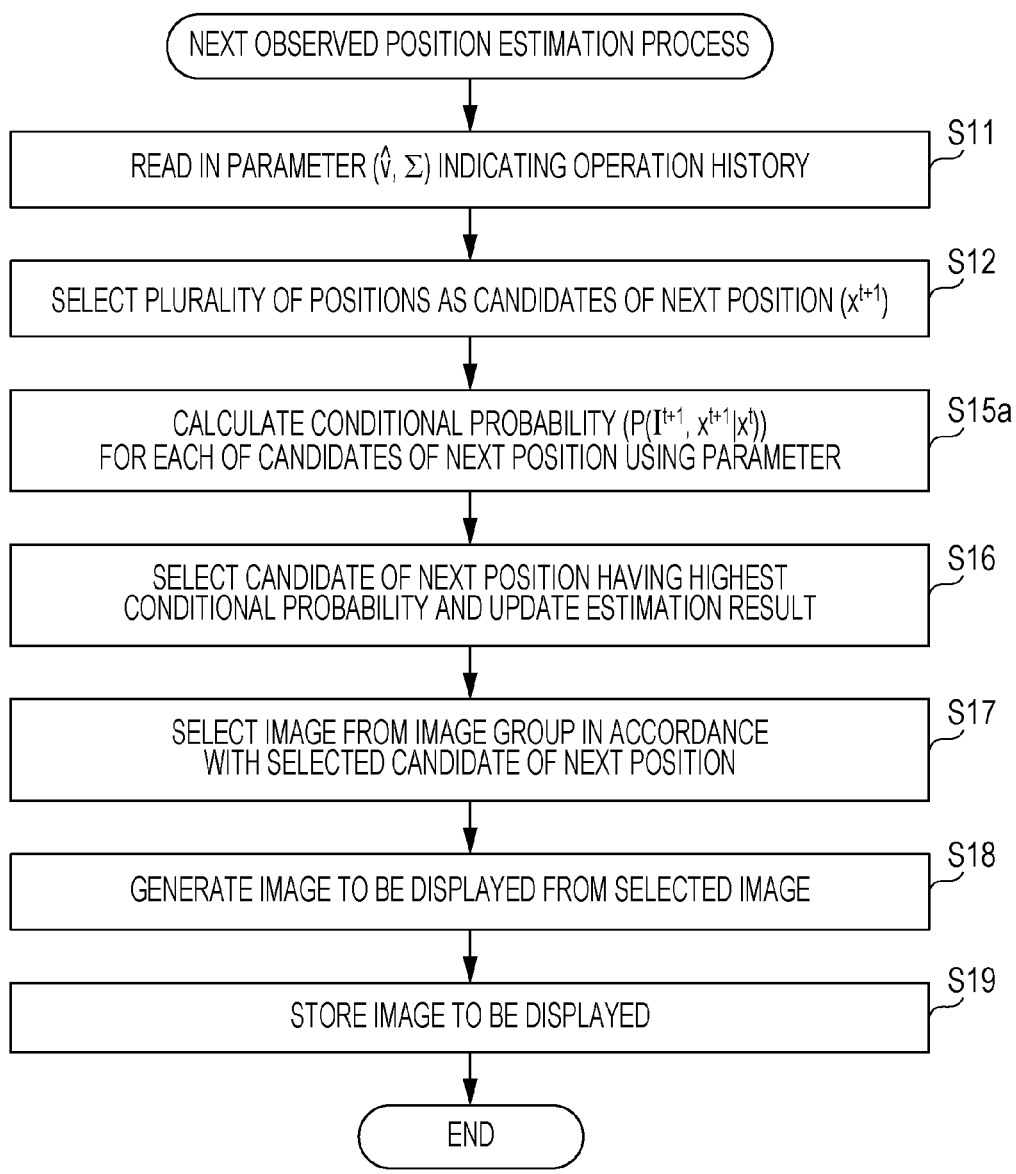
FIG. 17 is a flowchart of a process for obtaining the conditional probability using only information regarding the position.

FIG. 17 illustrates the procedure for obtaining the conditional probability using $v^t$ including only the information regarding the position. Unlike FIG. 2, steps S13 and S14 of FIG. 2 are removed from FIG. 17. In addition, step S15 in FIG. 2 is changed to step S15a. Hereinafter, the process performed in only step S15a is described. Description of the other processes is the same as that for FIG. 2.

In step S15a, the information regarding the scale factor is not used. The next observation estimating unit 101 calculates the conditional probability for each of the candidates of the next position using the parameters û and Σ.

Note that since the process for estimating the scale factor is not included, selection of an image having a different resolution is not needed in the image selection process performed in step S17. Accordingly, the image pyramid holding unit 108 need not hold an image group having different resolutions. It is only required that the image pyramid holding unit 108 holds at least one image. The displayed image generating unit 102 may generate, for example, an axillary image in which the candidate of the next position is visible (e.g., the square frames 705 to 707 illustrated in FIG. 9) as the image to be displayed.

However, when an image group having different resolutions is held and if the candidate of the next position is within a predetermined range from the current estimated position, the next observation estimating unit 101 may select a higher resolution. If the candidate of the next position is within a predetermined range from the current estimated position, it is highly likely that the pathologist attempts to observe the lesion in detail. Accordingly, it is appropriate that an image including the candidate of the next position and having a higher resolution be displayed.

The above exemplary embodiments and modifications have been described with reference to mainly, the image display system and the image processing apparatus and the block diagrams illustrated in FIGS. 1, 12, and 14. In reality, the systems and the apparatuses are realized by using a computer. Although the following description is given with reference to the image display system 100 and the image processing apparatus 110 illustrated in FIG. 1, the description can also apply to the image display system and the image processing apparatus illustrated in FIG. 12 and FIG. 14.

Figure 18:
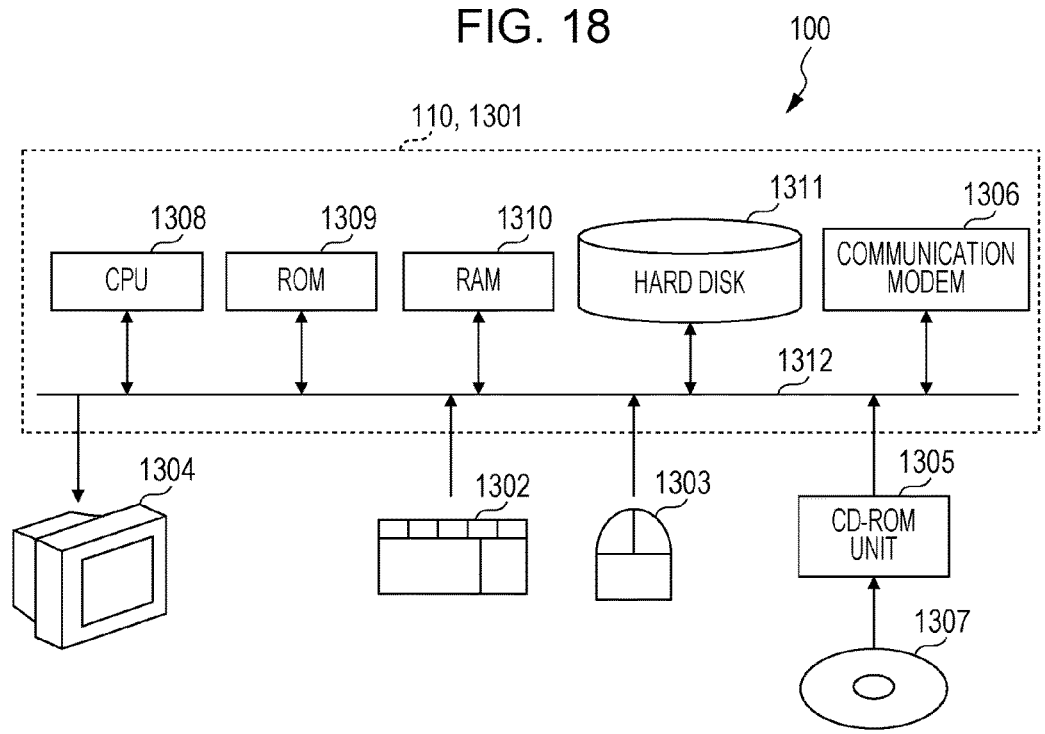
FIG. 18 is a block diagram of the hardware configuration of the image display system according to the first to third exemplary embodiments.

FIG. 18 is a configuration diagram of a computer that serves as the image processing apparatus 110 (refer to FIG. 1). By integrating a display with the computer, the image display system 100 can be achieved. That is, the image display system 100 includes a computer 1301 serving as the image processing apparatus 110, a keyboard 1302 and a mouse 1303 used by an operator to input an instruction to the computer 1301, a display 1304 used to present the information, such as the result of computation performed by the computer 1301, a compact disc-read only memory (CD-ROM) unit 1305 from which a program executed by the computer 1301 is read, and a communication modem 1306.

The keyboard 1302 and the mouse 1303 correspond to the input unit 104. The display 1304 corresponds to the image display unit 103 (refer to FIG. 1 and other drawings).

The program executed by the image processing apparatus 110 is recorded in a CD-ROM 1307, which is a computer-readable storage medium, and is read by the CD-ROM unit 1305. Alternatively, the program is read by the communication modem 1306 via a computer network.

The instructions that cause a central processing unit (CPU) 1308 to perform the operation indicated by the flowchart of the present disclosure are set forth in the program. That is, the CPU 1308 functions as the next observation estimating unit 101 and the displayed image generating unit 102. The CPU 1308 can function as each of the next observation estimating unit 101 and the displayed image generating unit 102 in accordance of the type of operation to be performed and the time at which the operation to be performed. Note that the CPU 1308 can also function as the super-resolution processing unit 901 (FIG. 12), the result display control unit 1101 (FIG. 14), and/or the magnifying operation determination unit 1102 (FIG. 14). A CPU may be provided so as to correspond to each of the constituent elements.

The computer 1301 includes the CPU 1308, a read only memory (ROM) 1309, a random access memory (RAM) 1310, a hard disk 1311, the communication modem 1306, and a bus 1312.

The CPU 1308 executes the program read through the CD-ROM unit 1305 and the communication modem 1306. The ROM 1309 stores a program and data required for the operation performed by the computer 1301. The RAM 1310 stores data such as parameters used during execution of the program.

The hard disk 1311 stores, for example, programs and data. The hard disk 1311 can function as the observation feature holding unit 106, the parameter holding unit 107, the image pyramid holding unit 108, and/or the generated image holding unit 109.

The communication modem 1306 communicates with another computer via a computer network. The bus 1312 connects the CPU 1308, the ROM 1309, the RAM 1310, the hard disk 1311, the communication modem 1306, the display 1304, the keyboard 1302, the mouse 1303, and the CD-ROM unit 1305 with one another.

Note that the keyboard 1302, the mouse 1303, and the CD-ROM unit 1305 connected to the computer 1301 may be removed if the display is of a touch panel type or the communication modem is used.

In addition, the present disclosure may be the above-described method. Furthermore, the present disclosure may encompass a computer program that realizes the method by using a computer and digital signals formed from the computer program.

Still furthermore, the present disclosure may encompass a non-transitory computer-readable recording medium, such as a flexible disk, a hard disk, a CD-ROM, an MO, a DVD, a DVD-ROM, a DVD-RAM, a Blu-ray Disc (BD™), or a semiconductor memory, that stores the above-described computer program or digital signals. Moreover, the present disclosure may encompass the digital signals stored in such a non-transitory recording medium.

In addition, in the present disclosure, the above-described program and digital signals may be transmitted via an electric communication network, a wireless or wired communication circuit, a network such as the Internet, or a data broadcast.

Alternatively, the present disclosure may be realized using another independent computer system by recording the above-described program and digital signals in the non-transitory recording medium and transporting the non-transitory recording medium or by transporting the above-described program and digital signals via, for example, the above-described network.

Figure 19:
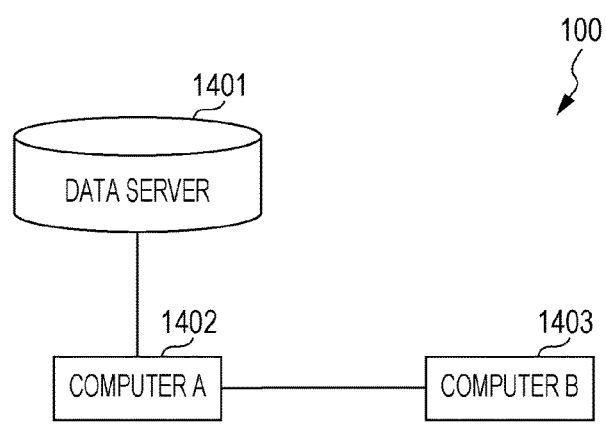
FIG. 19 illustrates an example of the configuration of the image display system formed from a data server and a plurality of computers.

Alternatively, as illustrated in FIG. 19, the image display system 100 may be achieved by using a plurality of computers and a data server. In the present disclosure, a data server 1401 may be separately provided. Thereafter, the data to be held by, for example, the estimation result holding unit 105, the observation feature holding unit 106, the parameter holding unit 107, and the image pyramid holding unit 108 are placed in the data server 1401. Subsequently, the information may be read out by a computer A 1402 via, for example, a network. The constituent elements corresponding to the image processing apparatus (e.g., the next observation estimating unit 101, the displayed image generating unit 102, and the super-resolution processing unit 901) may be included in a computer A 1402, while the image display unit 103, the generated image holding unit 109, the result display control unit 1101, the magnifying operation determination unit 1102, and the input unit 104 may be included in a computer B 1403. In this manner, the blocks of the image display system 100 may be separately included in the two computers. In addition, the number of the computers A 1402 that reads out the information from the data server 1401 is not necessarily one. A plurality of the computers A 1402 may be provided. Similarly, a plurality of the computers B 1403 may be provided.

In addition, the present disclosure may encompass an image processing method including the process described below.

Let "first position" be the "current position $x^{t}$" included in the first area. In the image processing method, a plurality of candidates of the position serving as "the candidates of the next position $(x^{t+1})_1, \ldots, (x^{t+1})_i, \ldots$" with respect to the "first position" are selected and acquired (step S12 illustrated in FIG. 2).

Figure 20:
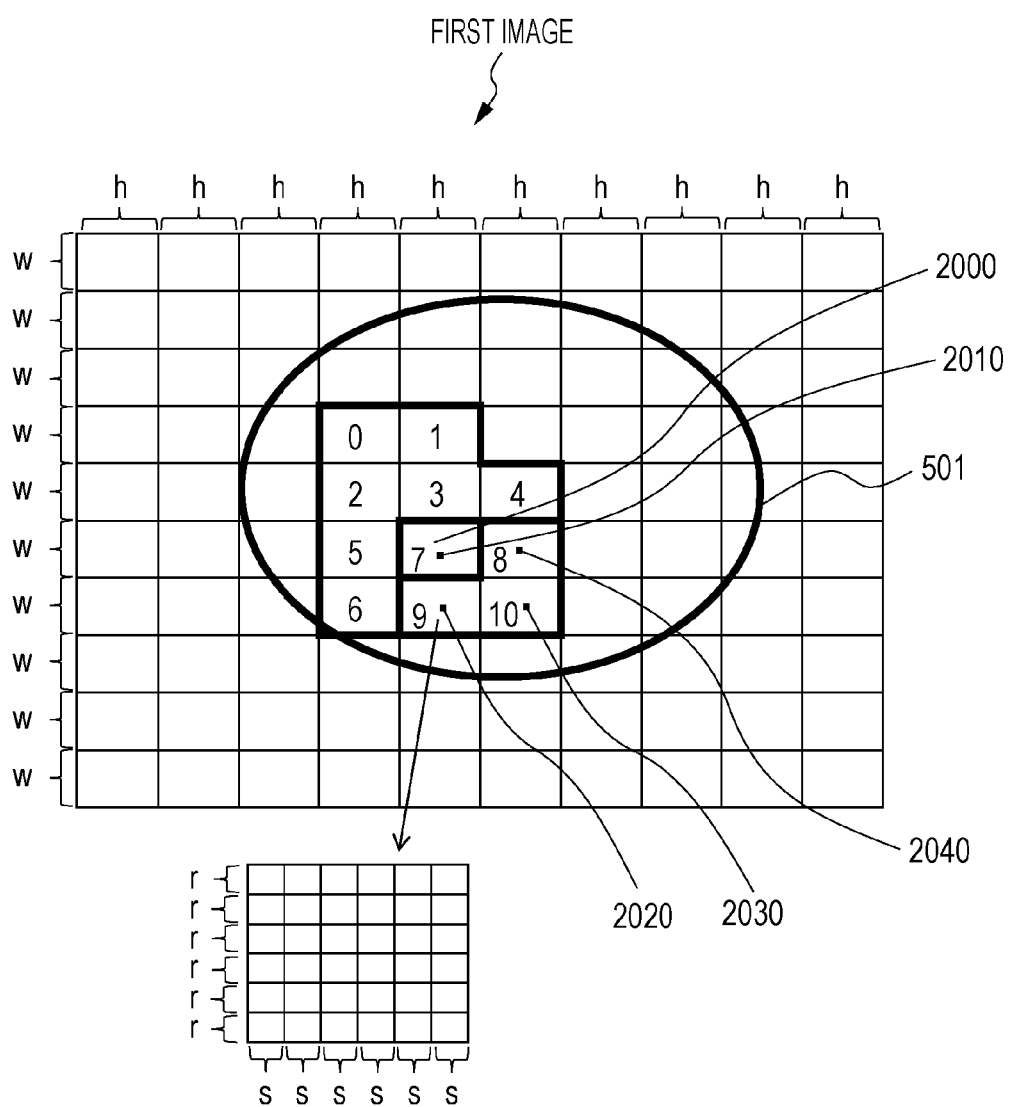
FIG. 20 illustrates an image processing method.

FIG. 20 illustrates the image processing method. FIG. 20 includes many parts that are similar to those in FIG. 7. Hereinafter, the items that are not illustrated in FIG. 7 are mainly described. For example, in FIG. 20, a first area 2000 is a rectangular area with the number "7" written in it. The first area 2000 includes a first position 2010 that is currently observed by the pathologist. The plurality of candidates of the position include a first candidate of the position 2020, a second candidate of the position 2030, and a third candidate of the position 2040. Note that in this example, a second area is an area including three rectangular areas (i.e., the rectangular area with the number "8", the rectangular area with the number "9", and the rectangular area with the number "10"). That is, the second area includes the plurality of areas including a third area formed from the rectangular area with the number "9" (i.e., the rectangular area with the number "8", the rectangular area with the number "9", and the rectangular area with the number "10"). The plurality of areas and the plurality of candidates of the position have a one-to-one correspondence, and each of the plurality of areas includes the corresponding candidate of the position. That is, the rectangular area with the number 8 corresponds to the third candidate of the position 2040, the rectangular area with the number 9 corresponds to the first candidate of the position 2020, and the rectangular area with the number 10 corresponds to the second candidate of the position 2030. In addition, the rectangular area with the number 8 includes the third candidate of the position 2040, the rectangular area with the number 9 includes the first candidate of the position 2020, and the rectangular area with the number 10 includes the second candidate of the position 2030. The third area is a rectangular area with the number 9, and the third area corresponds to the first candidate of the position 2020. The third area includes the first candidate of the position 2020. The second area is adjacent to the first area 2000. The second area does not include an area already observed by, for example, the pathologist (in this example, the areas with the numbers 0 to 6). The plurality of candidates of the position are included in the second area, which is different from the first area 2000. The first area 2000 and the second area are included in the same image, that is, a first image (an image having (10 h×10 w) pixel values).

The plurality of candidates of the position include the first candidate of the position 2020. The first candidate of the position 2020 is, for example, the candidate of the next position $(x^{t+1})_i$.

A first plurality of pixel values correspond to the first candidates of the position. That is, the area with the number 9, which includes the first candidate of the position 2020, has the first plurality of pixel values, which are the pixel values of a plurality of pixels ((6×r)×(6×s)) pixels). When the image is divided into 10 w×10 h rectangular areas, each of the plurality of candidates of the position is some position included in the rectangular area (w×h pixels) which is estimated to be selected by a user. For example, the candidate is a point at the upper left corner of the rectangular area. The plurality of pixel values corresponding to the candidates of the position are the pixel values of w×h(=(6×r)×(6×s)) pixels included in the rectangular area that includes the candidates of the position.

In the image processing method, image feature information regarding a plurality of pixels included in each of the plurality of areas is determined. That is, the "image feature information", which is the "image feature" of the first plurality of pixel values included in the rectangular area with the number 9 including the first candidate of the position 2020, is determined. The "image feature information", which is the "image feature" of the plurality of pixel values included in the rectangular area with the number 10 including the second candidate of the position 2030, is determined, and the "image feature information", which is the "image feature" of the plurality of pixel values included in the rectangular area with the number 8 including the third candidate of the position 2040, is determined (refer to, for example, S13 of FIG. 2 and S103 of FIG. 5). Note that the "image feature information of a plurality of pixel values included in each of the plurality of areas" can be also expressed as the "image feature information regarding each of the plurality of areas". This is because since the image feature information regarding any one of the plurality of areas can be uniquely determined, the image feature information regarding each of a plurality of pixel values included in the area can be regarded as the image feature information that is uniquely determined. That is, the "image feature information", which is the "image feature" of the rectangular area with the number 9 including the first candidate of the position 2020, is determined, the "image feature information", which is the "image feature" of the rectangular area with the number 10 including the second candidate of the position 2030, is determined, and the "image feature information", which is the "image feature" of the rectangular area with the number 8 including the third candidate of the position 2040, is determined (refer to, for example, S13 of FIG. 2 and S103 of FIG. 5).

The information including the information indicating the update history of the observed position for one or more images other than the first image, that is, the parameter (v^, Σ) indicating the operation history is acquired (step S11 of FIG. 2).

One of the plurality of candidates of the position is selected on the basis of the image feature information and the history information (step S16 of FIG. 2).

The first plurality of pixel values and the plurality of positions included in the third area have a one-to-one correspondence. That is, the area with the number 9 is the third area, and the 6 r×6 s pixel values included in the third area are the first plurality of pixel values.

The second area includes the third area. That is, in FIG. 20, the second area is the area including the area with the number 8, the area with the number 9, and the area with the number 10. In addition, the area with the number 9 is the third area.

In the following example, by using a classification method corresponding to the type of the first image, the first plurality of pixel values included in the third area, which is the area with the number 9, are classified to obtain a first classification result and, thereafter, the image feature information regarding the first plurality of pixel values included in the third area is determined on the basis of the first classification result. Note that by using a similar method, the image feature information regarding a plurality of pixels included in the area with the number 8 may be determined, and the image feature information regarding a plurality of pixels included in the area with the number 10 may be determined.

The first plurality of pixel values are classified first using the classification method corresponding to the type of the first image. That is, it is determined which type of local feature is used in accordance with the type of image (in the example illustrated in FIG. 7, it is determined that eight types of local feature, that is, "A", "B", "C", "D", "E", "F", "G", and "H" are used). Thereafter, it is evaluated by which one of the eight types of local feature each of the pixel values of r×s pixels is approximated. Such evaluation is performed for each of "r×s pixels" of 36 groups. In this manner, an image feature 1504 is obtained.

For example, let the first image be the image of some organ (e.g., the image of the lung). The local features "A", "B", "C", "D", "E", "F", "G", and "H" illustrated in FIG. 7 are applied to the image of the lung. However, in the case of the image of an organ other than the lung (e.g., the image of the heart), the pixel values may be classified by using the local features "I", "J", "K", "L", "M", "N", "O", and "P", which differ from the local features "A", "B", "C", "D", "E", "F", "G", and "H".

The image feature information of the first plurality of pixel values are determined on the basis of the result of classification.

The result of classification indicating that as illustrated in FIG. 7, the frequency of the local feature A=7, the frequency of the local feature B=4, . . . is obtained by using the local features "A", "B", "C", "D", "E", "F", "G", and "H" illustrated in FIG. 7. In this manner, the image feature 1504 is obtained.

The third area includes the first plurality of pixel values which are (6×r)×(6×s) pixel values. Let $a_{11}, \ldots, a_{ij}, \ldots a_{mn}$ be the first plurality of pixel values, where i, j, n, and m are natural numbers, 1≤i≤m=6×r, and 1≤j≤n=6×s. In addition, let $b_{11}, \ldots, b_{ij}, \ldots b_{mn}$ be a plurality of positions included in the third area. Furthermore, let $b_{11}, \ldots, b_{ij}, \ldots b_{mn}$ be the positions of the pixels corresponding to the pixel values $a_{11}, \ldots, a_{ij}, \ldots a_{mn}$, respectively (refer to FIG. 20 and FIG. 7).

When the first plurality of pixel values $a_{11}, \ldots, a_{ij}, \ldots a_{mn}$ are classified using the classification method corresponding to the type of the first image, that is, the local features "A", "B", "C", "D", "E", "F", "G", and "H", the classification is performed for each of r×s pixel value groups. Thus, 36 (=6×6) results of classification are obtained. Then, the obtained 36 results of classification serve as the image feature information regarding the first plurality of pixel values (refer to FIG. 7). While the above-described description has been given with reference to the third area including the first plurality of pixel values, which are (6×r)×(6×s) pixel values, the third area may include the first plurality of pixel values, which are (p×r)×(q×s) pixel values, where p, q, r, and s are natural numbers.

In addition, the above-described exemplary embodiments and modifications may be combined in any way.

The embodiments described in the present disclosure are to be considered in all respects only as illustrative and not restrictive. A value, a shape, a material, a constituent element, the positions and the connection form of the constituent elements, steps, and the sequence of steps used in the embodiments are only examples and shall not be construed as limiting the scope of the present disclosure. In addition, among the constituent elements in the embodiments described below, the constituent element that does not appear in an independent claim, which has the broadest scope, is described as an optional constituent element. The scope of the present disclosure is, therefore, indicated by the appended claims rather than by the foregoing description. All changes which come within the meaning and range of equivalency of the claims are to be embraced within their scope.

The technology according to the present disclosure is applicable to, for example, image measuring apparatuses that calculate the positive ratio from a pathological examination sample.

What is claimed is:

1. An image processing apparatus comprising:
a next observation estimator that estimates a position selected from among a plurality of position candidates using (i) operation history information including first information based on observed positions in an image under previous observations and (ii) information including estimation results for the plurality of position candidates, the estimated results being obtained on the basis of a probability value obtained from a predetermined probability distribution; and
a displayed image generator that generates an image to be displayed so that at least the estimated position is visually recognizable,
wherein the previous observations respectively correspond to the observed positions in the image,
wherein a total number of the previous observations is n, where n is a natural number greater than or equal to two,
wherein the observed positions in the image are respectively denoted as $(a_k, b_k)$, where k is a natural number from 1 to n, and wherein the first information includes (i) a value of $(a_1 + \ldots + a_k + \ldots + a_n)/n$ and (ii) a value of $(b_1 + \ldots + b_k + \ldots + b_n)/n$.

2. The image processing apparatus according to claim 1, wherein the predetermined probability distribution is a Gaussian distribution, and
wherein the estimation results respectively correspond to probability values, and the estimated position corresponds to a highest probability value from among the probability values.

3. The image processing apparatus according to claim 1, wherein the operation history further includes second information based on scale factors used at the observed positions,
wherein each of the scale factors indicates a magnification percentage or a reduction percentage of the image used when the image is observed,
wherein the scale factors respectively correspond to the observed positions in the image,
wherein the scale factors are respectively denoted $z_k$, where a scale factor zk corresponds to an observed position $(a_k, b_k)$,
wherein the second information includes a value of $(z_1 + \ldots + z_k + \ldots + z_n)/n$, and
wherein the next observation estimator calculates a scale factor for each of the plurality of position candidates.

4. The image processing apparatus according to claim 1, wherein the next observation estimator calculates image observation necessity levels of small areas including the plurality of position candidates using information regarding a pixel observation necessity level that is provided in advance for each of pixels of the image and that indicates a degree of necessity for observing the pixel, the image observation necessity levels respectively corresponding to the small areas, and the image observation necessity levels respectively corresponding the plurality of position candidates, and
wherein the next observation estimator calculates the probability value using corresponding image observation necessity level from among the image observation necessity levels.

5. The image processing apparatus according to claim 1, wherein the next observation estimator calculates the probability value by further using information regarding an image feature calculated in advance.

6. The image processing apparatus according to claim 1, wherein the displayed image generator generates an image used to display the estimation results.

7. The image processing apparatus according to claim 1, further comprising:
a super-resolution processor that determines whether a super-resolution process is performed on a partial image including the estimated position,
wherein if the next observation estimator determines that the super-resolution process is to be performed, the super-resolution processor generates a magnified image having an increased number of pixels on the basis of data of a plurality of images of a given pathological specimen captured while lighting the pathological specimen from different directions and performs the super-resolution process based on deconvolution on a small area corresponding to the partial image of the magnified image, the small area being including a plurality of small areas respectively corresponding to the plurality of position candidates.

8. An image display system comprising:
the image processing apparatus according to claim 1; and
an image display that displays the image.

9. An image display system comprising:
the image processing apparatus according to claim 3;
an image display that displays the image; and
a result display controller that performs control so that information regarding the estimated position and the scale factor is displayed.

10. The image display system according to claim 8, wherein the image processing apparatus further includes a super-resolution processor that determines whether a super-resolution process is performed on a partial image including the estimated position, and
wherein if the next observation estimator determines that the super-resolution process is to be performed, the super-resolution processor generates a magnified image having an increased number of pixels on the basis of data of a plurality of images of a given pathological specimen captured while lighting the pathological specimen from different directions and performs the super-resolution process based on deconvolution on a small area corresponding to the partial image, the small area being including a plurality of small areas respectively corresponding to the plurality of position candidates.

11. The image display system according to claim 10, wherein the image display displays an area subjected to a super-resolution process performed by the super-resolution processor so that the area is visually recognizable.

12. The image display system according to claim 11, further comprising:
an inputter that receives, from an operator, selection of a new region in the image,
wherein if the inputter receives selection of the new region, the result display controller instructs the next observation estimator to newly estimate the position using the selected region.

13. The image display system according to claim 12, wherein when the inputter receives selection of the new region in the image and if the selected region is not subjected to the super-resolution process, the result display controller instructs the super-resolution processor to perform the super-resolution process on the new region.

14. The image display system according to claim 13, further comprising:
a magnifying operation determinator that determines whether the operator has successively performed a predetermined number or more of magnifying operations on a region in the image,
wherein if determining that the operator has successively performed a predetermined number or more of a magnifying operation, the magnifying operation determinator instructs the super-resolution processor to perform the super-resolution process on the region.

15. An image processing method comprising:
estimating a position selected from among a plurality of position candidates using (i) operation history information including first information based on observed positions in an image under previous observations and (ii) information including estimation results for the plurality of position candidates, the estimated results being obtained on the basis of a probability value obtained from a predetermined probability distribution; and
generating an image to be displayed so that at least the estimated position is visually recognizable,
wherein the previous observations respectively correspond to the observed positions in the image, wherein a total number of the previous observations is n, where n is a natural number greater than or equal to two, wherein the observed positions in the image are respectively denoted as $(a_k, b_k)$, where k is a natural number from 1 to n, and wherein the first information includes (i) a value of $(a_1 + \ldots + a_k + \ldots + a_n)/n$ and (ii) a value of $(b_1 + \ldots + b_k + \ldots + b_n)/n$.

16. A non-transitory computer-readable recording medium storing a program that causes an apparatus including a processor to perform a process including:

estimating a position selected from among a plurality of position candidates using (i) operation history information including first information based on observed positions in an image under previous observations and (ii) information including estimation results for the plurality of position candidates, the estimated results being obtained on the basis of a probability value obtained from a predetermined probability distribution; and generating an image to be displayed so that at least the estimated position is visually recognizable, wherein the previous observations respectively correspond to the observed positions in the image, wherein a total number of the previous observations is n, where n is a natural number greater than or equal to two, wherein the observed positions in the image are respectively denoted as $(a_k, b_k)$, where k is a natural number from 1 to n, and wherein the first information includes (i) a value of $(a_1 + \ldots + a_k + \ldots + a_n)/n$ and (ii) a value of $(b_1 + \ldots + b_k + \ldots + b_n)/n$.

17. An image processing method comprising:

obtaining a plurality of position candidates for a first position included in a first area, the plurality of position candidates including a first position candidate, the plurality of position candidates being included in a second area other than the first area, the first area and the second area being included in a first image, the second area including a plurality of areas including a third area, the plurality of areas and the plurality of position candidates having a one-to-one correspondence, each of the plurality of areas including the corresponding position candidate, the third area corresponding to the first position candidate, the third area including the first position candidate;

determining image feature information regarding a plurality of pixel values of pixels included in each of the plurality of areas, the determination of the image feature information including determination of the image feature information regarding the first pixel values included in the third area;

obtaining history information indicating history of changing observed points for one or more images other than the first image; and determining one of the plurality of position candidates based on the image feature information and the history information, the one of the plurality of position candidates being observed immediately after an observation of the first position, wherein the plurality of pixel values of pixels included in each of the plurality of areas are classified by using a classification method corresponding to a type of the first image, wherein the image feature information regarding the plurality of pixel values of the pixels included in each of the plurality of areas is determined based on the classification result, wherein the first pixel values are classified by using the classification method corresponding to the type of the first image, and a first classification result is obtained, and wherein the image feature information regarding the first pixel values included in the third area is determined based on the first classification result.

18. The image processing method according to claim 17, wherein the number of the first plurality of pixel values is $(p \times r) \times (q \times s)$, where p, q, r, and s are natural numbers, wherein when the first pixel values are classified using the classification method corresponding to the type of the first image, the classification is performed for each of groups each including $(r \times s)$ pixel values to obtain $(p \times q)$ results of classification, and wherein each of the obtained $(p \times q)$ results of classification is defined as the image feature information regarding one of the first pixel values.

* * * * *